(12) United States Patent
McVey et al.

(10) Patent No.: US 7,070,930 B2
(45) Date of Patent: Jul. 4, 2006

(54) CHIMERIC VECTORS COMPRISING A PHAGE PACKAGING SITE AND A PORTION DERIVED FROM THE GENOME OF A EUKARYOTIC VIRUS

(75) Inventors: Duncan L. McVey, Derwood, MD (US); Douglas E. Brough, Gaithersburg, MD (US); Mohammed Zuber, Frederick, MD (US); Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 591 days.

(21) Appl. No.: 10/162,043

(22) Filed: Jun. 3, 2002

(65) Prior Publication Data

US 2003/0170899 A1    Sep. 11, 2003

Related U.S. Application Data

(60) Division of application No. 09/450,972, filed on Nov. 30, 1999, now Pat. No. 6,440,728, which is a continuation of application No. PCT/US98/12158, filed on Jun. 9, 1998.

(60) Provisional application No. 60/072,222, filed on Jan. 22, 1998, provisional application No. 60/049,072, filed on Jun. 9, 1997.

(51) Int. Cl.
*C12Q 1/68* (2006.01)
*C12N 5/00* (2006.01)
*C12N 5/02* (2006.01)
*C12N 15/00* (2006.01)
*C12N 15/09* (2006.01)

(52) U.S. Cl. .......... 435/6; 435/325; 435/320.1; 435/477

(58) Field of Classification Search .......... 435/6, 435/325, 320.1, 477
See application file for complete search history.

(56) References Cited

U.S. PATENT DOCUMENTS 6,027,722 A   2/2000   Hodgson
6,110,735 A   8/2000   Chartier et al.

FOREIGN PATENT DOCUMENTS

WO   WO 96/17070 A   6/1996
WO   WO 96/21007 A   7/1996
WO   WO 96/25506 A   8/1996
WO   WO 97/09439 A   3/1997

OTHER PUBLICATIONS

Chartier et al., *J. Virol.*, 70 (7), 4805-4810 (1996).
Ghosh-Choudhury et al., *Gene*, 50, 161-171 (1986).
Hardy et al., *J. Virol.*, 71 (3), 1842-1849 (1997).
Miyake et al., *PNAS USA*, 93, 1320-1324 (1996).
Pierce et al., *PNAS USA*, 89, 2056-2060 (1992).

*Primary Examiner*—James Ketter
*Assistant Examiner*—Konstantina Katcheves
(74) *Attorney, Agent, or Firm*—Leydig, Voit & Mayer, Ltd.

(57) ABSTRACT

The present invention provides an improved method of making eukaryotic gene transfer vectors comprising homologous recombining lambdid vectors with a second DNA in a bacterium to generate novel recombinant eukaryotic viral gene transfer vectors as well as a novel lambdid vector used in the inventive method and an inventive system comprising the novel lambdid vector.

6 Claims, 14 Drawing Sheets

CHIMERIC VECTORS COMPRISING A PHAGE PACKAGING SITE AND A PORTION DERIVED FROM THE GENOME OF A EUKARYOTIC VIRUS

CROSS-REFERENCE TO RELATED PATENT APPLICATIONS

This patent application is a divisional of U.S. patent application Ser. No. 09/450,972, filed Nov. 30, 1999, now U.S. Pat. No. 6,440,728 which is a continuation of International Application No. PCT/US98/12158, filed Jun. 9, 1998, which designates the United States and which claims the benefit of U.S. Provisional Patent Application No. 60/072,222, filed Jan. 22, 1998, and U.S. Provisional Patent Application No. 60/049,072, filed Jun. 9, 1997.

FIELD OF THE INVENTION

The present invention pertains to vectors constructed in a prokaryotic cell for use in gene transfer to eukaryotic cells, vectors useful for making eukaryotic gene transfer vectors, and methods of making the same.

BACKGROUND OF THE INVENTION

Gene transfer to eukaryotic cells has both in vivo and in vitro uses. As is well known, in vivo gene transfer to eukaryotic cells can be used to immunize a host, for therapeutic gene transfer to a host, and to study the biology of transferred genes in vivo. In vitro gene transfer to eukaryotic cells can be used to study simple and complex biological phenomena such as protein function, protein half-life, and gene-protein interactions. One preferred method for transferring genes to eukaryotic cells has been through the use of recombinant eukaryotic viruses. Although researchers and clinicians have enjoyed the many advantages of recombinant eukaryotic viruses for gene transfer to eukaryotic cells, the difficulty of constructing these viruses has impeded the rate at which new and useful gene transfer experiments and protocols have been developed.

Because of their large size, many recombinant eukaryotic viruses are produced via homologous recombination. Conventionally, homologous recombination used to generate large viral vectors has taken place in a host eukaryotic cell permissive for the growth of the recombinant virus (see, e.g., Berkner, *BioTechniques*, 6, 616–628 (1988)). Homologous recombination in eukaryotic cells, however, has at least two major drawbacks. The process is time consuming, and many preferred recombinant eukaryotic viral constructions are at a selective disadvantage relative to the predecessor eukaryotic viruses from which they are obtained. Therefore, if a skilled artisan attempts to create a new recombinant virus through the lengthy process of homologous recombination in a eukaryotic cell and fails to create the desired virus, that artisan is often unable to readily distinguish between the need to modify the construction technique and the possibility that the desired virus vector is not viable in the host cell. Accordingly, there is a need for new methods of generating eukaryotic gene transfer vectors.

Previous improvements in the generation of gene transfer vectors have included the use of yeast-based systems (Ketner et al., *PNAS USA*, 91, 6186–6190 (1994)), plasmid-based systems (Chartier et al., *J. Virol.*, 70, 4805–4810 (1996); Crouzet et al., WO 96/25506), and cosmid-based systems (Miyake et al., *PNAS USA*, 93, 1320–1324 (1996)). While these systems can expedite the production of new recombinant eukaryotic viruses, additional flexibility and selection pressures are desired. The present invention provides a rapid and flexible method for producing new vectors, which can be used in gene transfer to eukaryotic cells in vitro and in vivo. The present invention also provides vectors modified for use in eukaryotic gene transfer, as well as methods and systems for using the same. These and other advantages of the present invention, as well as additional inventive features, will be apparent from the description of the invention provided herein.

SUMMARY OF THE INVENTION

The present invention provides a DNA vector comprising a portion of a eukaryotic viral genome comprising an ITR, a regulatable negative selection gene (NSG) or a stringently regulated growth discrimination gene (SRG), and a phage packaging site. The present inventive vector preferably comprises a full eukaryotic (e.g., adenoviral) amplicon. Moreover the regulatable negative selection gene or growth discrimination gene is preferably embedded within the portion of the eukaryotic viral genome of the present inventive vector such that a double recombination event with a second DNA vector removes the regulatable negative selection gene or growth discrimination gene at the same time that a DNA of interest is transferred into the present inventive vector. In another embodiment of the present inventive vector a positive selection gene is proximal to the NSG, which forms a dual selection cassette (DSC). The combination of negative and positive selection genes forms a dual selection cassette (DSC) that provides the skilled artisan with exquisite control of the homologous recombination system. The SRG can serve either a negative or positive selective function, or both. Accordingly, it is useful to have an SRG proximal to either a PSG or an NSG. SRGs that are adjacent or proximal to another selective gene are termed dual discrimination cassettes. Of course, the present inventive vector can also comprise other genetic elements, such as an independent positive selection gene that is not positionally associated with the NSG, DSC, or SRG and a bacterial origin of replication.

The present inventive vector optionally comprises additional advantageous elements. For example, the present inventive vector optionally comprises a deficient or conditionally deficient lambdoid origin of replication, which enhances the effectiveness of double homologous recombination. The present inventive vector is preferably configured such that the phage packaging site is proximal to an ITR of a eukaryotic viral amplicon, which allows for direct generation of an amplicon when the present inventive vector is encapsidated and transduced or infected into a suitable eukaryotic cell.

The present invention also provides for a library comprising or consisting of a multiplicity of the present inventive vector comprising a multiplicity of genetic elements that may be the same or different.

The present invention also provides a system for the generation of recombinant DNA vectors. Any embodiment of the present inventive vector can constitute a portion of the present inventive system. The present inventive system comprises at least a second DNA that comprises two DNA segments each of which have sufficient homology to the inventive vector to mediate homologous recombination and which flank or surround a DNA that is desirable to incorporate into the present inventive vector or into a portion of the eukaryotic viral DNA or amplicon that forms a portion of the present inventive vector. Certain embodiments of the present inventive system comprise a third DNA that can complement in trans a deficiency in a lambdoid origin of replication and, optionally, a fourth DNA that expresses a source of phage capsids that encapsidate intermediate or product vectors comprising the phage origin of replication. Either or both of the third and fourth DNAs of the inventive system can be optionally incorporated into the genome of a bacterial cell.

The present invention also provides a method of making and packaging a DNA vector. The inventive method comprises transfecting a bacterial cell with two DNA vectors that undergo homologous recombination to form a desired DNA vector. One vector comprises a phage packaging site, and an NSG, DSC, or SRG that is flanked by two DNA segments that mediate a double homologous recombination event with the second vector employed in the system. The double homologous recombination event places a DNA into the first vector and simultaneously removes the NSG, DSC, or SRG, and introduces a DNA from the second vector into the first vector. The method also includes the use of in vivo conditions that encapsidate the double homologously recombined product that contains a phage packaging site into a phage capsid. The present inventive method can also comprise infecting the encapsidated product vector into a population of cells under conditions such that the negative selection gene is active prior to harvesting the product vector from a lysate of the second cell, which serves to eliminate cells containing undesired DNA constructs from the population of cells from which the product vector is isolated.

The present inventive method optionally employs a first vector comprising a deficient or conditionally deficient lambdoid origin of replication. In this embodiment of the present invention, the deficiencies in the lambdoid origin of replication are complemented in trans during the period of time in which the homologous recombination event occurs, which enhances the effeciency of the process for several reasons.

The present invention also provides an improved method of gene transfer to eukaryotic cells. The improved method comprises using lambdid vectors (defined below) to generate novel recombinant vectors including recombinant eukaryotic viral vectors, that are capable of transferring genes to eukaryotic cells. Lambdid vectors, or portions thereof, also can be transduced into eukaryotic cells without the aid of (eukaryotic viral or phage) coat proteins. Lambdid vectors transduced into eukaryotic cells can generate new recombinant eukaryotic viral vectors, direct heterologous gene expression, or be used for other purposes. Additionally, lambdid vectors can be encapsidated into lambdoid capsids comprising chimeric lambdoid coat proteins capable of binding to eukaryotic cells. These lambdid vectors encapsidated into recombinant capsids can be used to directly transduce eukaryotic cells.

These and other features of the present invention are more fully described below.

BRIEF DESCRIPTION OF THE DRAWINGS

FIG. 4 also depicts the interrelationship of the DNA constructs when used in one embodiment of the present inventive method.

In FIG. 10 a first vector and a second vector undergo double homologous recombination to form a product vector. The product vector is isolated from other vector forms by the application of positive and negative selective pressure and by the use of phage encapsidation and infection.

DETAILED DESCRIPTION OF THE INVENTION

Definitions

Figure 1:
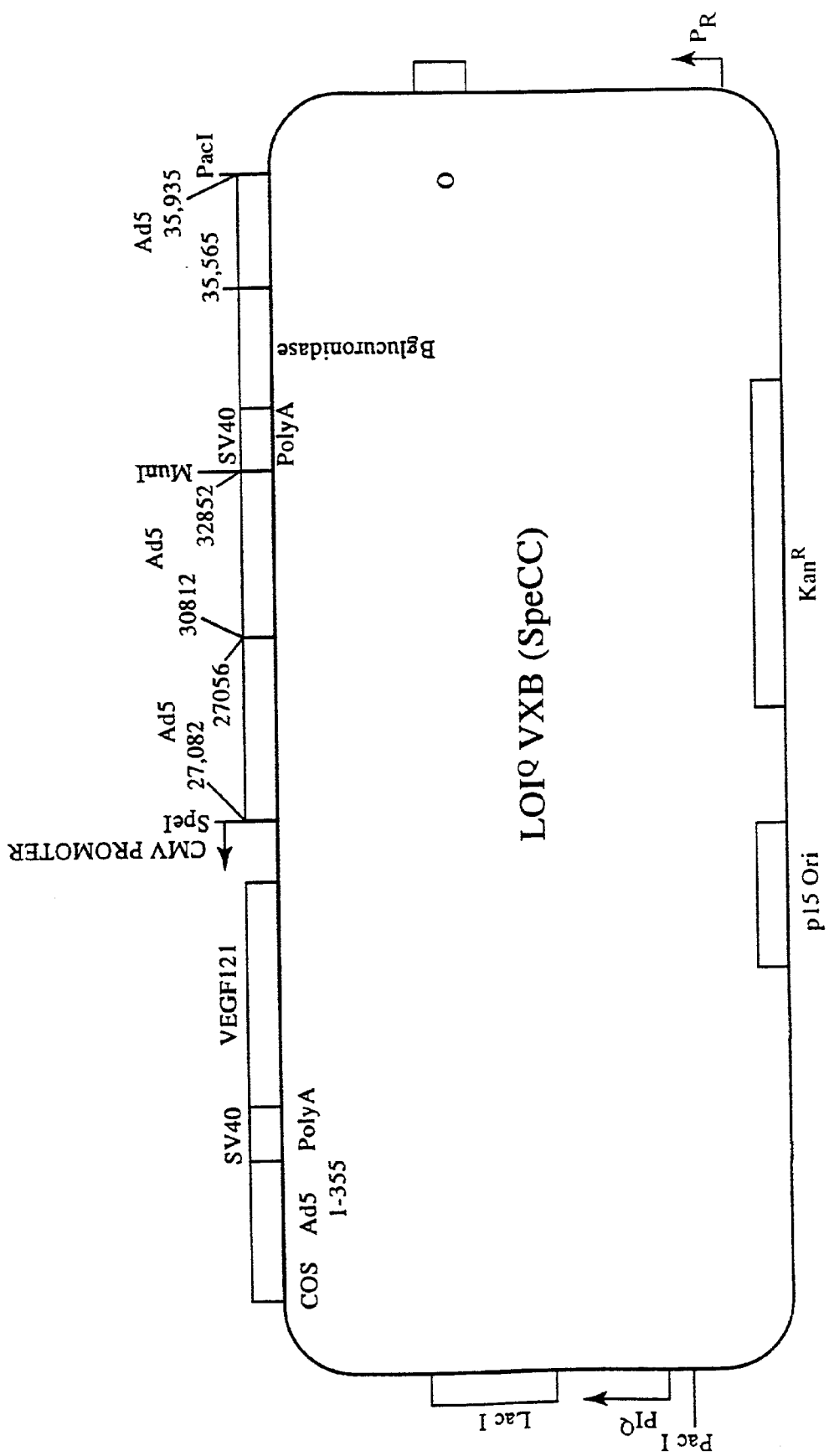
FIG. 1 depicts the lambdid vector $LOI^Q VXB(SpeCC)$.

Certain terms are used with particular meaning, or are defined for the first time, in this description of the present invention. For the purposes of the present invention, the following terms are defined by their art-accepted definitions, when such exist, except that when those definitions conflict or partially conflict with the definitions set forth below. In the event of a conflict in definition, the meaning of the terms are first defined by the definitions set forth below.

Transfected means any suitable method of transferring a DNA from the outside of a cell to the inside of a cell so that the cell remains biologically viable. Suitable methods of transfection include, but are not limited to, infection, chemical transformation, electroporation, microparticle bombardment, and other techniques known in the art.

The term lambdoid is an art-accepted adjective that denotes that the noun it modifies is of a phage having a high degree of similarity to bacteriophage Lambda. In contrast, the term lambdid vector refers to certain embodiments of the present inventive DNA vector. Lambdid vectors are so-named because they comprise an operon that comprises a lambdoid origin of replication. One preferred embodiment of a lambdid vector is described in detail in Example 8 below.

An amplicon is a vector capable of replicating and being packaged when any deficient essential gene functions are provided in trans. A eukaryotic viral amplicon includes at least a portion of each terminal repeat required to support the replication of the viral DNA and the DNA required to encapsidate the genome into a viral capsid. Eukaryotic viral amplicons preferably comprise at least about 90% of the full ITR sequence.

In certain embodiments of the present invention, bacteria are transferred from a liquid culture medium to solid culture medium ("plated") in such a manner that individual bacteria grow to form clonal colonies of a single bacterium from the liquid culture. The skilled artisan will appreciate that colonies appear at variable rates when a mixture of bacteria are plated and some bacteria have a growth advantage relative to the other bacteria in the culture. Those bacteria that grow rapidly and form visible colonies of at least about 2 mm in diameter before other colonies appear are called primary colonies. Colonies that are not clearly visible to the naked eye for at least about twelve hours, and preferably at least about 30 hours, after the clear appearance of primary colonies are called secondary colonies.

A stringent promoter is one that is not recognized by an E. coli or other bacterial host RNA polymerase, but rather by a polymerase that recognizes only a small family of highly homologous DNA sequences. Stringent promoters are typically phage promoters, e.g., the T7 promoter, the T3 promoter, and the Sp6 promoter.

The abbreviations NSG, DSC, SRG, PSG, and DDC are used herein to denote negative selection gene, dual selection cassette, stringently regulated gene, positive selection gene, and dual discrimination cassette. These terms are defined below.

The term anti-selective gene comprises NSGs and SRGs which substantially inhibit the growth of cells comprising the same, when the gene is activated. DSCs comprise NSGs and, therefore, also comprise anti-selective genes.

The term comprising is used in the description of the invention and in the claims to mean "including, but not necessarily limited to".

The term embedded when applied to DNA vectors is used to refer to sequences which are inserted into or in place of the sequence in which they are embedded. Embedded sequences can be adjacent to spacer sequences. Spacer sequences that form a portion of an embedded sequence are preferably less than about 250 base pairs in length and preferably do not encode for a biological function. The term adjacent when applied to DNA vectors refers to sequences that are separated by less than about 30 base pairs. Adjacent sequences are preferably separated by less than about 12 base pairs.

The Invention

Double homologous recombination has been conventionally used to make large DNA vectors. The present invention provides, inter alia, a DNA vector, and a system for making a recombinant DNA vector, that enables the present inventive method, which comprises using double homologous recombination, to take place in bacteria with an unprecedented ease and with an ability to affirmatively control the reaction that produces the desired vector.

The present invention provides a method of making and packaging a recombinant DNA vector. The inventive method comprises transfecting a bacterial cell with two DNA vectors that undergo homologous recombination to form a desired DNA vector. One vector (i.e., the acceptor or first vector) comprises a phage packaging site, and an anti-selective gene (an NSG, SRG, DSC, or DDC) that is flanked by two DNA segments that mediate a double homologous recombination event with the second vector employed in the system. The double homologous recombination event produces a desired product vector by introducing a DNA from the second vector into the first vector and simultaneously transferring the anti-selective gene from the first vector to the second vector. The product vector advantageously comprises a phage packaging site. In that regard, the method preferably includes the use of in vivo conditions that encapsidate the product vector made by the double homologous recombination into a phage capsid. The present inventive method preferably continues by infecting the encapsidated product vector into a population of cells (which population is different from the cell in which the homologous recombination occurs) under conditions such that the anti-selective gene is active prior to harvesting the product vector from a lysate of the second cell, which serves to eliminate cells containing undesired DNA constructs from the population of cells from which the product vector is isolated.

The present inventive method optionally employs a first vector comprising a lambdoid origin of replication. The lambdoid origin of replication is preferably a deficient or conditionally deficient lambdoid origin of replication. However, the advantage of the lambdoid origin of replication is mainly derived from its operation during the double homologous recombination of the present inventive method. This replication enhances the efficiency of the process by providing an elevated rate of homologous recombination and by providing greater amounts of DNA. The deficiencies in the lambdoid origin of replication are complemented in trans during the period of time in which the homologous recombination event occurs. Various deficient lambdoid origins of replication are described herein below as well as methods of activating these origins. Moreover, as discussed below it is advantageous to prevent lambdoid replication during the remainder of the present inventive method. Accordingly, the employment of a deficient or conditionally deficient lambdoid origin of replication constitutes one preferred embodiment of the present invention.

Various embodiments and improvements of the present inventive method exist and are dependent, in part, upon the design of the present inventive vector, either alone or in combination with the design of the second inventive vector. Other embodiments of the present inventive method are dependent upon the inclusion of a helper phage or lysogen, and upon the characteristics of the cell or population of cells used to carry out the present inventive method.

The present inventive DNA vector (i.e., the first or acceptor vector) comprises (i) a portion of a eukaryotic viral genome comprising an ITR, (ii) a regulatable negative selection gene (NSG) or a stringently regulated growth discrimination gene (SRG), and (iii) a phage packaging site. The present inventive vector preferably also comprises at least one origin or replication that is operable in a bacterial cell. This origin may be any suitable origin but is preferably a low copy number, non-phage origin to enhance the stability of the vector. A preferred bacterial origin is the pBR322 origin. Other suitable origins include, but are not limited to, p15A, pSC101, and RK2.

The portion of the eukaryotic viral genome of the first vector can also contain a second ITR, which creates an amplicon lacking a packaging site. Instead of, or in addition to a second ITR, the portion of the eukaryotic viral genome can also comprise a eukaryotic viral packaging site. Thus, the first vector optionally contains a eukaryotic viral amplicon.

The present inventive vector is preferably circular, because such vectors are generally easier to propagate and maintain in bacteria.

As stated above, the present inventive vector comprises an anti-selective gene, which can be either a regulatable NSG or an SRG. In certain embodiments of the present invention, the anti-selective gene is embedded within the portion of a eukaryotic vector of the first vector. This is particularly useful, when a terminal portion of the eukaryotic viral genome is not to be replaced by the double homologous recombination event so that when the double homologous recombination event takes place the anti-selective gene is removed from the product vector. However, the anti-selective gene does not need to be embedded within the eukaryotic viral genome in those instances when a region outside the eukaryotic viral genome of the first vector participates in the homologous recombination. In either embodiment, the present inventive vector is designed such that the double recombination event with a second DNA vector removes the anti-selective gene at the same time that a DNA of interest is transferred into the present inventive vector to form the product vector.

In another embodiment of the present inventive vector a positive selection gene (PSG) is placed proximally to or adjacent to the anti-selective gene. The combination of negative and positive selection genes forms a dual selection cassette (DSC) that provides the skilled artisan with exquisite control of the homologous recombination system. For example, in the process of forming the present inventive vector, the positive selection gene can be used to select for colonies of bacteria that harbor the PSG and therefore the DSC comprising the NSG. Additionally, the PSG of the DSC can be used to generate selective pressure against vector forms that spuriously recombine or otherwise change to eliminate the NSG. In each of these embodiments, an SRG can be substituted for a NSG of the DSC.

Of course, the present inventive vector can also comprise other genetic elements, such as an independent positive selection gene that is not positionally associated with the NSG, DSC, or SRG and a bacterial origin of replication. An independent positive selection gene is not removed from the present inventive vector by the double homologous recombination event. Preferably, the independent PSG is not embedded within the portion of the eukaryotic viral genome that resides in the present inventive vector. The independent PSG is useful for, inter alia, providing positive selection pressure for bacteria harboring a desired product vector obtained from homologous recombination between a vector comprising an NSG or DSC and another vector.

The PSG of the DSC (when applicable) and the independent PSG can be any suitable gene. A PSG comprises a DNA encoding an RNA or a protein that provides a selective growth advantage to bacteria expressing the positive selection gene product under definable conditions. Antibiotic resistance genes and auxotrophy complementing genes are examples of positive selection genes suitable for use in the present invention. Suitable PSGs that confer antibiotic resistance to a host cell include, but are not limited to, kanamycin, ampicillin, tetracycline, and zeocin resistance genes. Tetracycline and zeocin genes function better than other PSGs in some embodiments of the present invention and have functioned as well as any other PSG tested in other embodiments of the present invention. That is, bacterial cells harboring DNA vectors of the present invention are less prone to becoming mucoidal and are often more susceptible to the NSG, when the genes encoding resistance to tetracycline and/or zeocin are incorporated into the present inventive vector, than when the genes encoding ampicillin or kanamycin resistance are incorporated into the present inventive vector. Therefore, it is often preferable to use tetracycline and zeocin resistance genes for the PSG(s) of the present invention.

Figure 6:
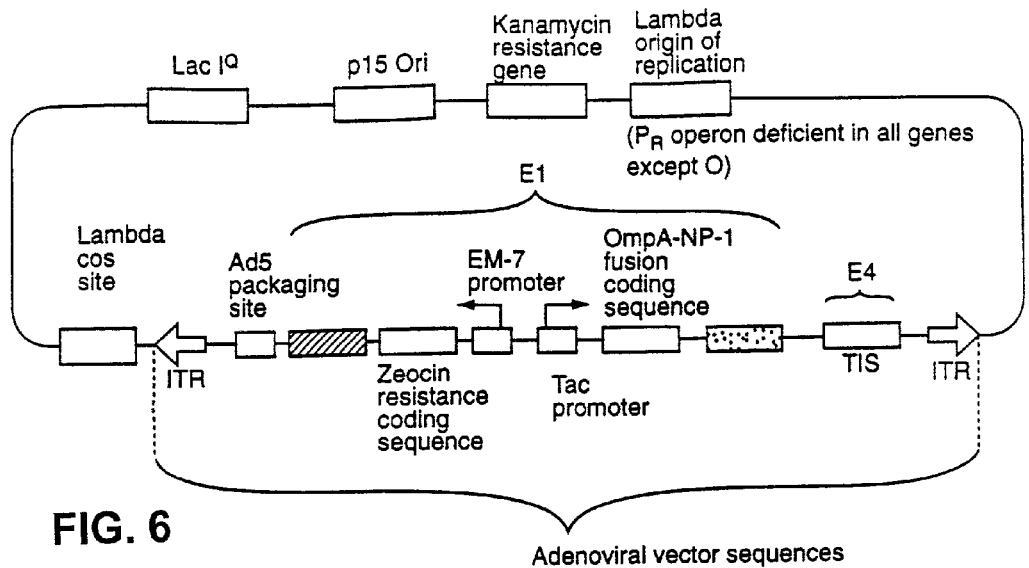
FIG. 6 depicts one embodiment of Vector 7, a lambdid vector of the present invention.

The positive selection gene promoter can be any suitable promoter, but it will be appreciated that a constitutive promoter is preferable for many embodiments of the present invention, at least inasmuch as the artisan then need not attend to the function of the positive selection gene promoter. In a DSC, the positive selection gene promoter is preferably positioned and/or oriented so that it does not promote transcription of an RNA encoding the negative selection gene product (i.e., does not promote transcription of a sense-strand RNA of the negative selection gene). This can be accomplished, inter alia, by placing the positive and negative gene promoters in a 5' to 5'(or back to back) orientation, such that transcription starts at each promoter and proceeds away from the other, as is depicted in FIG. 6.

Additionally, the second vector of the present invention can comprise a PSG. The PSG of the second vector is preferably different than the DSC-associated PSG (when present), or the independent PSG, of the present inventive vector.

The NSG of the present invention comprises a DNA encoding a negative selection gene product and, operably linked thereto, a negative selection gene promoter, as well as other elements required for the transcription and translation (if appropriate) of a negative selection gene product. The negative selection gene product is any RNA or protein that can confer a strong growth disadvantage to a host cell expressing it or, preferably, that causes the death of a host expressing it under definable conditions.

Suitable negative selection genes include, but are not limited to, NP-1, sacB, ccd genes (e.g., ccdB), a tetracycline gene (tet$^R$), par genes (e.g., parD), and Kid. Suitable NSGs also include fusion proteins of these genes (e.g., genes comprising portions of these genes fused to portions of the genes encoding thioredoxin, β-galactosidase, the OmpA signal sequence, luciferase, protein A or any other suitable fusion partner). Suitable NSGs also include active variants of the aforementioned genes, which can comprise deletions, mutations, or other modifications. In short, a suitable NSG provides for the death or substantial decrease in the growth rate of a bacterium expressing the same. A discussion of NSGs can be found in chapter 22 of *Escherichia coli* and *Salmonella*, 2$^{nd}$ edition (Niedhardt ed.), (ASM press, 1996), particularly on pages 2317–2318.

By way of further illustration and not limitation, it is noted that the DNA encoding an OmpA FLAG/NP-1 fusion protein is illustrative of an NSG that is useful in the context of the present invention. The OmpA FLAG/NP-1 gene product is a rat defensin fusion protein that lacks its cognate signal sequence and further comprises the OmpA signal sequence and a Flag M1™ or Flag M2™ antibody (Eastman Kodak). The production of an OmpA FLAG/Np-1 fusion protein in a bacterium renders that bacterium non-viable. While not intending to be bound by any particular theory, one explanation for the negative selection action of OmpA FLAG/Np-1 is that the OmpA signal localizes the NP-1 portion of the protein in, or proximally to, a bacterial membrane such that the NP-1 portion of the protein forms pores in that membrane and destroys the host cell's viability.

The sacB gene is illustrative of another NSG that is useful in the context of the present invention. The sacB gene-product converts sucrose (when provided in the growth medium) to leaven. Leaven is highly toxic to bacteria. The sacB NSG can be regulated by providing or withholding sucrose from a bacterial host that constitutively expresses sacB.

The negative selection gene promoter can be strongly regulatable (i.e., inducible, suppressible, or both inducible and suppressible) so as to provide control over the negative selection pressure that the NSG provides. Alternatively, if the NSG promoter is not regulatable, then a suitable means for preventing the function of the negative selection gene must be used. Suitable means for controlling the function of an NSG include, but are not limited to, withholding or providing a substrate that the NSG product converts into a toxin (e.g., sucrose for the sacB gene) or providing in trans a powerful regulator of the negative selection gene product or promoter (e.g., T7 RNA polymerase).

The Tac promoter (a Trp and Lac hybrid promoter that is well known in the art) is repressible by the Lac I protein and inducible by IPTG, and is illustrative of a suitable negative selection gene promoter that is especially useful when the activity of the NSG product is not regulatable (e.g., with OmpA FLAG/NP-1). To achieve a sufficient level of control over the Tac promoter, it is preferable to use this promoter in combination with a bacterial strain that overexpresses the repressor protein (e.g., a LacI$^Q$ strain) or to provide the LacI$^Q_g$ gene on a vector in the bacterial cell.

The stringent promoter operably linked to an open reading frame comprising a strong signal for the initiation of translation serves a similar function as the NSG of other embodiments of the present invention. When the stringent promoter is activated, e.g., by placing it in a cell that is expressing a stringent polymerase, the stringently regulated gene produces a strong stress on the host cell. As a consequence, plated colonies of that cell are substantially growth retarded. If a host cell comprising an activated stringently regulated gene is plated from a culture comprising identical or nearly identical cells that do not comprise an active stringently regulated gene, then that host cell will either not form colonies or give rise only to secondary colonies which can easily be segregated from those cells giving rise to primary colonies. This is routine for those skilled in the art. For example, the primary colonies can be re-plated or streaked onto a second solid growth medium so that individual colonies on the second growth medium comprise only cells giving rise to primary colonies. Optionally, additional routine steps can be taken to decrease the probability of secondary colony supporting cells from contaminating cultures of those cells that form primary colonies. This routine process is more fully known as pure-culturing.

Advantageously, an SRG can function both as a selective and anti-selective gene (as a dual-discrimination gene). For example, a gene comprising an EM-7 promoter and encoding zeocin resistance protein or encoding a lacZ-zeocin resistance fusion protein can be incorporated into the present inventive vector. The DNA fragment comprising the EM-7 promoter actually contains two promoters. One promoter is a constitutive promoter recognized by bacterial host cell polymerases. Embedded within the DNA fragment comprising the EM-7 promoter is a T7 promoter, which is recognized only by T7 RNA polymerase. In a cell lacking the T7 RNA polymerase, this SRG provides a strong positive selective pressure in the presence of zeocin or zeocin analogues. Thus, the SRG is a PSG. However, when this SRG is placed in a cell expressing T7 RNA polymerase, the SRG expression causes the cell to grow very slowly or to die. T7 polymerase can be constitutively or inductively expressed from the bacterial genome or a plasmid in the cell, or can be provided by superinfection with a phage. Thus, this SRG can be used to select for cells comprising the SRG by adding zeocin or a zeocin analogue to the growth medium and can be used to anti-select cells comprising the SRG by ensuring that T7 RNA polymerase is expressed in the cells. While applicants do not wish to be bound by any particular theory, it is believed that the stringent RNA polymerase has a substantially higher affinity for nucleotides than host RNA polymerases and that when the T7 RNA polymerase directs the expression of the SRG the host cell's metabolic processes are so depleted that the growth rate of the cell is severely attenuated. This action appears to be much stronger when the RNA transcript of the T7 polymerase directs the translation of a substantial open reading frame (ORF)(at least about 15 amino acids in length, but preferably greater than about 30 or 100 amino acids in length) and when the ORF is preceded by a strong Shine-Dalgarno sequence.

Optionally, the embodiments of the present inventive vector that comprise a dual-discrimination site (such as the EM-7-lacZ-zeo SRG discussed above) can also comprise a PSG or NSG located adjacent to or proximal to the SRG to form a DNA segment that is analogous to the DSC described above. If a PSG is adjacent to the SRG, then the SRG preferably encodes an anti-selective gene product, a marker gene product, or other gene product of interest since any positive selective effects of the SRG would be merely redundant. However, if the SRG encodes for a gene product that provides positive selective pressure for a cell expressing it, then the SRG is optimally placed adjacent to an NSG, which can be used to amplify the negative selective pressure on cells comprising and expressing the DDC.

The present inventive vector and second vector are preferably configured such that the phage packaging site is proximal to an ITR of a eukaryotic viral amplicon of the product vector. In many embodiments of the present invention this is easily achieved by placing the phage packaging site proximally to the (first) ITR of the first (present inventive) vector. Such a configuration allows for direct generation of an amplicon when the product vector is encapsidated into a phage capsid and transduced or infected into a suitable eukaryotic cell. This is true because many phage linearize DNA to be packaged and because if an ITR or LTR is suitably proximal to a free terminus of a DNA that comprises a eukaryotic viral amplicon, and that linear DNA is delivered to a eukaryotic cell permissive for the replication of the eukaryotic amplicon, then replication of the eukaryotic viral amplicon can occur. By proximal, it is meant within about 250 base pairs, preferably within about 100 base pairs, and more preferably within about 25 base pairs.) In other words, proximity of an ITR or LTR to a packaging site allows for the replication of the eukaryotic viral DNA/vector in a eukaryotic cell without the need to linearize or cut the DNA with restriction enzymes prior to transfection into the eukaryotic cell.

The present invention also provides an improved method of gene transfer to eukaryotic cells. The improved method comprises using lambdid vectors (defined below) to generate novel recombinant vectors including recombinant eukaryotic viral vectors, that are capable of transferring genes to eukaryotic cells. Lambdid vectors, or portions thereof, also can be transduced into eukaryotic cells without the aid of (eukaryotic viral or phage) coat proteins. Lambdid vectors transduced into eukaryotic cells can generate new recombinant eukaryotic viral vectors, direct heterologous gene expression, or be used for other purposes. Additionally, lambdid vectors can be encapsidated into lambdoid capsids comprising chimeric lambdoid coat proteins capable of binding to eukaryotic cells. These lambdid vectors encapsidated into recombinant capsids can be used to directly transduce eukaryotic cells.

An embodiment of the present inventive method comprises transducing a lambdid vector comprising a negative selection gene and Vector 8 (defined below) or another suitable DNA into bacteria that are susceptible to infection by a lambdoid phage (e.g., lambda), culturing the transduced bacteria under conditions that are selective for the lambdid vector (or, preferably, selective for the lambdid vector and Vector 8), and infecting the culture with a helper phage. The vectors homologously recombine, generating a bacterial culture that comprises bacteria carrying a population of vectors, including reactant vectors, desired product-vectors, and undesired product-vectors. Some of these vectors (within the bacteria) are packaged into capsids. The present inventive method facilitates the isolation of those product-vectors which are desired by applying selective mechanisms (e.g., resistance to antibiotics, preferential capsid packaging, etc.). Although the desired product-vectors are likely to be generated at only a very low frequency in each population, means for automatically selecting the desired vectors are incorporated into the present inventive method.

As noted above, the present inventive vector optionally comprises a lambdoid origin of replication, which enhances the effectiveness of double homologous recombination. Also as noted above, the operon comprising a lambdoid origin of replication is preferably conditionally inoperative. Conditional inoperability of the origin of replication provides a number of advantages including, but not limited to, the prevention of "runaway" replication. In one embodiment of the inventive lambdid vector, a DNA segment can be taken from a lambdoid phage and modified such that at least one essential gene required for the operation of the lambdoid origin of replication is deficient or conditionally deficient. The deficient essential gene function can be of the phage or of the host, but is preferably of the phage. For example, the operon can contain a gene encoding for an important replicative gene required for the operablity of the origin (which is not redundant on the vector). In this case, a deletion can be made in an essential region of the DNA encoding a replicative gene function or a mutation in the DNA encoding the gene function can be made that encodes a frameshift mutation in the amino terminal portion of the gene product. Alternatively, an essential gene function can be conditionally eliminated such that the lambdoid origin of replication becomes conditionally inoperable. The deficient or conditionally deficient gene is preferably one derived from the phage, and most preferably a replicative gene of the phage (e.g., O or P of lambda), so that the deficiency or conditional deficiency does not significantly impair normal bacterial host metabolism, propagation, or function. Additionally, as will be discussed below, the lambdoid origin of replication can be made conditionally inoperable by placing it under the control of a tightly and inducibly regulated promoter.

When it is desirable for the lambdoid origin of the lambdid vector to be operable, the deficiency or conditional deficiency in the essential gene function required for the operability of the origin can be complemented in trans, inducibly in cis from a separate operon of the lambdid vector, or inducibly in cis from within the operon (e.g., by changing the growth conditions such as by shifting incubator temperature from restrictive to permissive). An operon in the context of the present invention is an active or activatable promoter and the DNA sequences encoding the RNA transcribed by the promoter. The transcription of RNA is important because it is required for suitably efficient DNA replication originating at the lambdoid origin of replication. However, the RNA transcribed from an operon does not necessarily encode a protein.

The lambdoid origin of replication can similarly be taken from any other suitable lambdoid phage or be highly homologous to the same. Exemplary lambdoid phage include any of the group having an immunity defined by the lambdoid phage lambda, 21, φ80, φ81, 82, 424, and 434. Of course, the origin can be taken from any of these prototypical phage themselves. Additionally, the origin of replication may be synthesized by methods that are well known in the art.

The lambdoid origin of replication suitable for use in the context of the present invention can be from lambda. The DNA sequence of lambda is publicly available in the Genbank database (accession symbol LAMCG) and elsewhere. The coordinates of suitable DNA fragments of lambda include (1) 37,951–39,591 with a deletion of 38,041–38,653 (i.e., the $P_R$ promoter through gene O with Cro-CII deleted), (2) 38,663–39,591 (i.e., all of the O gene and some flanking sequences), (3) 39,004–39,200 (a relatively small conditionally operable origin), and (4) 39,004–39,173. The skilled artisan will be aware of the O protein binding sites (iterons), the A/T rich region and the dyad symmetry sequence downstream of this site (usually comprising an Eco RI site). It will be appreciated that more efficient operation of the present invention can be obtained by including one or more iterons and the dyad symmetry sequence in the lambdoid origin, although depending on the context of the DNA construct, these sequences can be deleted or altered.

In addition to the wild type origin sequence, a modified lambda sequence can also be used. For example, coordinates 39,095–39,118 can be deleted, which unconditionally inactivates the origin. When a "G" residue is inserted into the deleted region and the "A" residue at position 39,076 is deleted, the operability of the origin caused by the first mutation is reversed and an operable, modified lambda origin of replication is obtained. With this modified origin of replication, the following DNA segments form origins of replication useful in the context of the present invention: (5) 38,663–39,591 (contains all of gene O and some flanking sequences), (6) 39,004–39,200 (a smaller DNA that contains all the binding sites and symmetry sequences of the origin), and (7) coordinates 39,004–39,173 (which is a relatively small origin that retains the ability to respond to O and P).

Other lambdoid origins of replication can be used as well. For example, a DNA comprising coordinates (8) 3,253–5,159 having been deleted of coordinates 3,355–4,148 of the Phi80 (Genbank Accession Symbol BP80ER) sequence is useful in the context of the present invention. This sequence contains the $P_R$ promoter through the O gene with the sequences comprising the Cro through the CII genes being deleted. Useful smaller fragments of this sequence include coordinates (9) 4,188–5,159 (the O gene and some flanking sequences), (10) 4,567–4,764 (all origin binding sites and some flanking sequences), and (11) 4,567–4,727 (which is a relatively small origin fragment). In addition to the origins described above, the origin can be derived from Phi82. For example, the following sequence (12) is from Phi82 and useful in the context of the present invention.

```
                tacgcgcatt gcaaatgagt tgctggaagc  30  SEQ ID NO:1
tgtgatgctg gccggattaa cacagcacca gcttctggtc ttcctggctg  80
tcatgcgcaa aacatatggc tttaataaaa aactggattg ggtgagcaac 130
gagcaacttt ccgagttgac cgggatattg ccgcacaagt gttctgctgc 180
aaaaagcgtt ctggtaaagc gtgggattct tattcagagc gggcggaata 230
tcggcattaa taatgtggtc agtgaatggt caacattacc cgaatcaggt 280
aagaaaaata aagtttacct gaaagaggta aatttacctg aatcaggtaa 330
aaaaagttta cccaaatcag gtaaaggcgt ttacccgaat caggtaaaca 380
caaaagacaa actaacaaaa gacaatataa aaccttttc gtccgagaat 430
tctggcgaat cctctgacca accagaaaac gatcttc.              465
```

Additionally, (13) coordinates 235–467 and (14) 235–432 of this sequence are also useful in the context of the present invention. Of course, the examples of suitable origins of replication given above illustrate the present invention, but are not meant to limit it. Additionally, some of these sequences comprise the $P_R$ promoter, while others do not comprise a promoter. It will be appreciated that each of these origins require transcription to support DNA replication and that a suitable promoter is to be provided. Further information regarding lambdoid origins of replication can be obtained from Moore et al., "Sequence organization of the origins of DNA replication in lambdoid coliphages", *Gene*, 14, 91–101 (1981); Grosschedl et al., "DNA sequences and structural homologies of the replication origins of lambdoid bacteriophages", *Nature*, 277, 621ff, (1979); Moore et al., "Dissection and Comparative Anatomy of the origins of replication of lambdoid phages", *Cold Spring Harbor Symp. Quant. Biol.*, 43 (pt1), 155–163 (1979); Rybchin, "Genetics of bacteriophage φ80—a review", *Gene*, 27, 1–11 (1984); and Campbell, "Comparative molecular biology of lambdoid phages", *Ann. Rev. Microbiol.*, 48, 193–222 (1994).

The phage packaging site of the present inventive vector can be from any phage. The lambdoid origin of replication, if included, is preferably obtained from the same phage as the phage packaging site but also can be obtained from a different lambdoid phage or a non-lambdoid phage (e.g., T7). The packaging site can be selected from any phage but is chosen, in part, to accommodate the size of the lambdid vector. For example, T7 capsids package a smaller genome than lambda capsids. Therefore, if a T7 packaging site is incorporated into the present inventive vector, then a smaller vector can be efficiently packaged into the relatively smaller capsid of T7. In contrast, if a lambda packaging site is incorporated into the present inventive vector, then the lambdid vector can be much larger without substantially reducing the efficiency of packaging. The lambda packaging site, cos, is among those phage packaging sites preferred in the context of the present invention.

The packaging site also can be selected to comport with the use of particular phage coat proteins. For example, chimeric T7 coat proteins having affinity for eukaryotic cells can be made. If it is desired to package the present inventive vector into a capsid comprising such a chimeric T7 coat protein, then it is preferable to use a T7 packaging site in the present inventive vector. Similarly, incorporation of a chimeric lambda protein dictates that the present inventive vector comprises a lambda packaging site.

A lambdid vector preferably does not comprise all of the structural genes of a lambdoid phage, and can contain no phage structural genes. In some embodiments of the present invention, the only lambdoid sequences contained in the lambdid vector are those of the O gene of Lambda comprising the Lambda origin of replication. In still other embodiments, the only lambdoid sequences of the lambdid vector are the lambdoid origin of replication and a lambdoid phage packaging site. Consequently, a lambdid vector usually has the capacity to carry a substantial amount of non-lambdoid DNA and still be efficiently encapsidated into a phage capsid.

In contrast to other embodiments of the present inventive vector, lambdid vectors need not have, and can be used without, a constitutively functional origin of replication.

However, a constitutively functional origin of replication allows for the stable maintenance of the lambdid vector in a bacterial cell. Therefore, a source of the deficient or conditionally deficient gene function necessary for the operability of the lambdoid origin of replication can be constitutively supplied in a bacterium comprising the lambdid vector. Under such circumstances, the lambdid vector can be maintained in the bacterium by the lambdid origin of replication. However, lambdoid origins of replication can be unstable. Moreover, the result of continuous operation of the lambdoid origin could mediate runaway replication. These effects can be deleterious. Therefore, a lambdoid vector can advantageously comprise a second origin of replication which functions independently of the lambdoid origin or replication. Preferably, the second origin of replication is of a bacterial origin.

A library comprising a multiplicity of the present inventive vector also can be obtained. The inventive vector library can be constructed from a population of DNA sequences comprising a multiplicity of eukaryotic genetic elements or amplicons. Alternatively, the inventive lambdid vector can be homologously recombined with a population of DNA sequences with each DNA of the population comprising a DNA segment having high homology to the lambdid vector, preferably having high homology to the eukaryotic amplicon. It will be appreciated that these libraries have a multiplicity of utilities including the study of functional genomics (e.g., identifying the functions and identities of genomic and complementary DNA sequences), viral vector design, structure-function studies of individual genes or gene products, and more.

Any suitable promoter can be linked to the DNA segment comprising the lambdoid origin of replication. Examples of suitable promoters include the trp operon promoter, the tRNA$^{tyr}$ promoter, the Tet promoter, the lac operon promoter, the recA promoter, the lexA promoter, the T7A3 promoter, and synthetic promoters (e.g., a TTGACA sequence at the−35 region and a TATAAT sequence at the−10 region). These promoters can be used with or without the regulatory regions that naturally accompany them.

One preferred embodiment of the present invention comprises an operon containing a lambdoid origin of replication that is driven by the $P_R$ promoter of lambda (i.e., about sequence coordinates 38,041 to 40,284 of Genbank Accession Symbol LAMCG). The $P_R$ operon drives the transcription of the operon comprising the origin of replication in wild-type lambda and can be incorporated into a lambdid in its entirety, but is preferably rendered deficient or conditionally deficient in at least one gene function required for operability of the origin of replication. Some allowable and preferable modifications of the $P_R$ operon are discussed directly below.

The P protein encoded by the P gene of the $P_R$ operon is normally required in the assembly of the phage replication complex at the lambda origin. However, when expressed at high levels, P can interfere with host genome and plasmid replication. Additionally, P encodes a gene function required for the operability of the lambdoid origin of replication. Therefore, a recombinant lambdid phage vector comprising the lambda $P_R$ operon is preferably deficient or conditionally deficient in at least the gene encoding P.

Other gene functions that can be deficient in a lambdid vector comprising the lambdoid operon include the functions of Cro, CII, tR, O, and Oop transcription.

Cro autoregulates the $P_R$ promoter. This autoregulation of PR can be disadvantageous. If the PR promoter is used to drive transcription of the lambdid operon comprising the lambdoid origin of replication or if a lambdoid helper phage or lysogen (see, e.g., Example 8) is introduced into the bacterial host cell, cro can suppress $P_R$ of the helper phage or lysogen in trans. Thus, recombinant lambdid vectors comprising PR are also preferably deficient in the Cro gene.

CII is responsible for inducing the expression of CI. CI also down regulates $P_R$. If a second vector (e.g., a helper phage or lysogen) comprising the CI gene that is CII inducible is introduced into the cell, expression of the CI protein from the second vector will be rapidly induced by the CII expressed from the lambdid vector and interfere with the desired function of the $P_R$ promoter. Thus, the operon comprising the lambda origin of replication is preferably also deficient in CII.

The $P_R$ promoter directs transcription through (in order) cro, $tR_1$, CII, O, and P. The O gene comprises the origin of replication. $tR_1$ terminates transcription from $P_R$ before it gets to the origin of replication, unless the anti-terminator N protein acts at the nutR (N utilization site). Thus, $tR_1$ could block or impair the function of the lambdoid origin of replication. Therefore, the operon preferably also lacks the $tR_1$ transcription terminator or, alternatively, is used in conjunction with a helper virus that will express the N gene.

The O gene comprises the origin of replication. Therefore, if the O gene is deleted entirely, then a lambdoid origin of replication must be re-inserted into the operon. Alternatively, the production of the O protein can be prevented without deleting the O gene, e.g., by causing a frameshift mutations or the like. Additionally, transcription of the Oop RNA can be inhibited.

In another embodiment of the present invention, a promoter can be linked to a DNA comprising a lambdoid origin of replication, wherein the entire operon does not encode a protein. If the lambdoid origin of replication is from lambda, O and P proteins must be supplied in trans or inducibly from another locus of the vector, because the lambda origin of replication requires the presence of O and P to function.

The present invention also provides a gene transfer system. Any of the preceding lambdid vectors can constitute a portion of the present inventive gene transfer system useful for (1) functional genomics (e.g., finding a function for an expressed sequence tag (EST) or identifying binding peptides from a library), (2) therapeutics (e.g., neovascularization or antisense RNA delivery), and (3) general research (e.g., site directed mutagenesis driven study of the structure-function relationships of a steroid receptor or other protein) and the like.

In addition to the present inventive lambdid vectors, the present inventive system comprises a source of gene functions necessary to encapsidate lambdid vectors and a source of gene functions necessary to complement the deficiency or conditional deficiency of the lambdoid origin of replication. These sources are preferably encoded by a nucleic acid, which is preferably DNA, but also can be RNA. Additionally, these sources can be encoded by one DNA or by multiple DNAs. For example, the deficient or conditionally deficient gene functions required for the operability of the lambdoid origin of replication can be provided in trans by the host bacterium (i.e., the bacterial genome or plasmids/episomes maintained within the host cell), a helper phage, or a lysogen, or in cis from a separate regulatable promoter located on the lambdid vector. For ease of use, however, these gene functions are preferably provided by a phage or lysogen which also directs the encapsidation of the recombined lambdid. Alternatively, encapsidation gene products (including at least the D gene product when a lambda packaging site is used and including at least the gene 10 protein when a T7 packaging site is used) can be provided by a helper virus or packaging extract (such as Gigapack™ packaging extracts, Stratagene). However, it should also be understood that lambdid vectors can be used without encapsidation.

In one embodiment of the present inventive system, the source of the gene products allowing lambdoid replication and packaging of the lambdid vector is in a non-competing helper lambdoid phage. To prevent competition with the lambdid, the helper phage can be made replication and/or packaging deficient. For example, when the lambdid vector comprises a phage origin of replication operably linked to the $P_R$ promoter and is deficient in the gene encoding P and no other gene function essential for the replication of the phage, the helper phage can supply P and the packaging components. If the helper phage is a lambda phage, then it preferably is a phage that produces clear plaques. Lambda phage of this phenotype are known in the art as lambda clear and are widely available. To reduce packaging efficiencies, the helper phage can lack a packaging site. This can be achieved, for example, by placing parallel lox sites around the packaging site(s). Therefore, if the system is employed in a bacterial cell expressing cre, the helper phage will undergo cre-lox mediated destruction of its packaging capability and will serve as a source of P and packaging proteins for the lambdid vector. The cre in this case can be supplied in trans (e.g., by a co-transfer of a plasmid or be supplied inducibly in cis).

Another embodiment of the present inventive system employs phage packaging components obtained from a defective lysogen. A defective lysogen can be made from a phage genome by introducing a modification into the genome and establishing lysogeny. The modification can, for example, reduce the lysogenic phage genome to less than about 73% of its wild-type size. This modification makes the lysogen defective in packaging because, in general, phage genomes must be between 73% and 110% of a wild-type phage size. Alternatively, the defective lyosgen can be a lambda vector lacking a packaging site. Another alternative modification is to make one or more temperature-sensitive or suppressible amber mutations in an essential gene function of the helper phage. Preferably, the temperature-sensitive or suppressible amber mutation is not complemented by the lambdid vector. One way to prevent complementation is to use a lambdid vector having phage genetic elements obtained from a phage that has a different immunity than the helper phage.

A recombinant eukaryotic viral amplicon or genome obtained through double homologous recombination according to the present inventive method or system can be isolated, purified, and transduced into a eukaryotic cell which is permissive for the growth of the (complete or replication-deficient) eukaryotic virus, irrespective of whether it has been encapsidated. This is advantageous for at least two reasons. The skilled artisan can know a'priori that a correctly constructed eukaryotic genome has been transduced into a eukaryotic cell. Thus, if a recombinant virus does not propagate in that eukaryotic cell, the skilled artisan can be confident that the problem is not related to the lack of a proper recombination event. Additionally, large amounts of the eukaryotic viral genome can be quickly obtained prior to any use of a eukaryotic cell, thereby substantially accelerating the rate at which new eukaryotic viral stocks are obtained.

Encapsidation of the product vector and other vectors of the present invention facilitate certain uses of the vectors and storage of the vectors by protecting the DNA from the laboratory or clinical environment and can provide other advantages. Other advantages can be obtained by encapsidating the lambdid vector. For example, encapsidation can be used to linearize the lambdid vector (as disclosed above) resulting in a terminal eukaryotic viral ITR or LTR, which (as described above) is advantageous when the lambdid is transduced into a eukaryotic cell. Additionally, encapsidation allows the incorporation of a modified coat protein into the capsid to allow targeting of cells that are not normally transduced by the capsid (e.g., eukaryotic cells).

A modified coat protein, similar to those described in U.S. Pat. No. 5,559,099 (Wickham et al.), and U.S. Pat. No. 5,712,136 (Wickham et al.), International Patent Application WO 98/07877, U.S. Pat. No. 5,846,782 (Wickham et al.), and International Patent Application WO 97/20051, can redirect the targeting of the phage particle to a target cell such as a cell located in, or obtained from, a eukaryotic organism (e.g., a human).

At the genetic level, the gene encoding the D protein (or another phage coat protein) can be modified by inserting DNA encoding a non-native amino acid sequence specific for a cell surface structure, a receptor (including cell surface liposaccharides and the like), an antibody, or an epitope. For the D protein, the insertion of the non-native sequence can be at the amino and/or carboxyl terminus (i.e., within about 10, preferably 3, amino acids of either terminus). Alternatively at the protein level, lambda D coat protein or other phage coat proteins can be chemically (i.e., covalently) or transiently (i.e., through biological interactions) modified by a bispecific molecule. Such a bispecific molecule has affinity for the lambdoid coat protein (whether modified or not), and (i) a cell surface structure, (ii) a receptor (including cell surface liposaccharides and the like), (iii) an antibody, or (iv) an epitope. The bispecific molecule can cross-link the vector with a target cell, thereby facilitating its uptake and expression.

One alternative to the lambda capsid comprising a chimeric D protein is the T7 capsid and a chimeric gene 10 protein. A chimeric gene 10 protein preferably has a non-native amino acid at its carboxyl terminus.

An encapsidated recombinant lambdid vector that is targeted by a modified coat protein to a eukaryotic cell and comprises a eukaryotic genetic element has many uses including use as an in vitro or in vivo gene transfer vector. Of course, if the cell is a plant cell, the cell wall must first be permeablized, preferably by use of enzymes capable of digesting the cell wall. For example, a recombinant phage comprising such a chimeric coat protein having an RGD sequence (or a constrained RGD sequence), can be used to target the lambdid or phage vector directly to a target cell having an αv integrin. The chimeric coat protein mediates binding to the surface of the eukaryotic cell and the encapsidated lambdid vector or recombinant phage genome is internalized in an endosome. Through the internalization process, the encapsidated DNA becomes substantially free of the capsid proteins that surround it, so that each genetic element capable of being expressed in a eukaryotic cell can be transcribed and (if appropriate) translated. The targeted vector is preferably internalized with an endosomolytic agent. Endosomolytic agents induce the rupture of endosomes and significantly increase the efficiency of expression of vectors taken up by endosomes. Chloroquine, calcium phosphate particles, adenoviral coat proteins (including adenoviral virions), and adeno-associated viral coat proteins (or virions) are illustrative of useful endosomolytic agents.

The lambdid vector can contain a site-directed recombination system such as flp-frt or cre-lox. Using the cre-lox system as an example, a gene capable of being expressed in a eukaryotic cell (e.g., a promoter operably linked to a $VEGF_{121}$ cDNA and an SV40 polyadenylation signal) can be placed adjacent to a eukaryotic episomal origin of replication (e.g., the EBV latent origin of replication, ori P), which together are flanked by parallel lox sites. When both the vector and endosomolytic agent complex are contacted to a cell that allows the function of the origin (e.g., a cell expressing the EBNA-1, which is required for operation of the EBV Ori P origin of replication as in Raji cells) and cre protein (the expression of cre also can be carried out in the phage genome under suitable conditions), they are internalized into an endosome and the vector is unencapsidated. The endosome is lysed by the endosomolytic agent allowing the unencapsidated vector to be acted upon by the cre protein. The cre protein acts on the site-directed recombination sites and effects the excision of a circular DNA comprising the genetic element capable of being expressed and the EBV ori (i.e., an episome). In the case of the EBV Ori P, EBNA-1 expressed within the cell facilitates the long term maintenance of the episome. Of course, the episome expresses only the genetic elements it carries (e.g., $VEGF_{121}$). The remainder of the lambdid vector eventually is lost from the cell, provided that it lacks a functional eukaryotic origin of replication. Thus, starting with a lambdid vector of the present invention, a eukaryotic cell can be (1) specifically targeted, (2) genetically modified to contain an episome, and (3) caused to express the protein encoded by the episome in the host. Significantly, gene transfer according to this method need not be accompanied by the expression of phage or viral gene products in the targeted eukaryotic cell. Therefore, the targeted cell is less vulnerable to an immune response and is minimally altered at the genetic level.

Optionally, an episomal vector (as described herein) can contain one or more DNA segments or genetic elements which are homologous to a eukaryotic host genome such that the expression cassette can be transferred into the host genome by homologous recombination. In that case, the elements that allow for integration of the expression cassette into the genome of the eukaryotic cell can obviate the requirement for an origin of replication that functions in a eukaryotic cell.

A lambdi vector also can be used to generate a replication-deficient eukaryotic virus in a suitable cell that does not complement for the replication deficiency of the eukaryotic virus and to support the replication of the vector. (A suitable eukaryotic cell for the production of a replication-deficient virus of a particular type is any cell that supports the production of a wild-type eukaryotic virus, and in this case does not complement the deficiency of the replication-deficient virus itself.)

Figure 5:
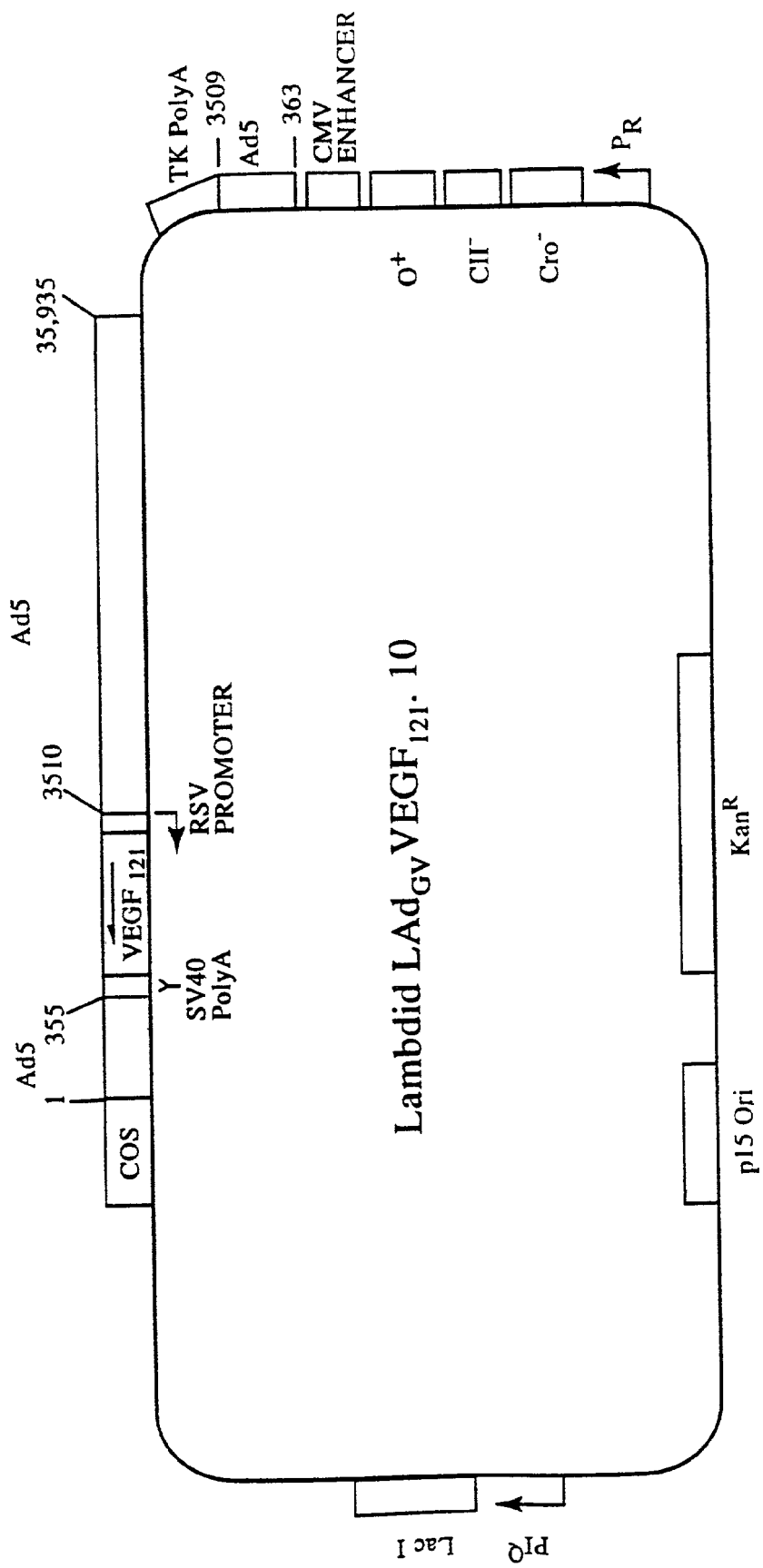
FIG. 5 depicts lambdid vector $LOI^Q VX\text{-}Ad_{GV}VEGF_{121}\text{-}10$. This vector can be encapsidated in a gene D-modified lambda capsid to produce an encapsidated DNA vector comprising an adenovirus carrying an expression cassette for $VEGF_{121}$. The encapsidated vector can be contacted with a eukaryotic cell having a receptor or ligand specific for the chimeric gene D coat protein. The eukaryotic cell will then take up the encapsidated vector. If the eukaryotic cell is permissive for the replication of the adenoviral vector that is a part of the encapsidated lambdid vector, then a stock of adenoviral vectors can be obtained from the cell. Irrespective of the ability of the DNA vector to replicate in the eukaryotic cell, the $VEGF_{121}$ passenger gene can still be expressed in the cell.

In this embodiment, the lambdid vector comprises a genome of a eukaryotic virus comprising a deficiency in at least one (essential) gene function required for replication. The replication deficient viral genome preferably also comprises a passenger gene of interest and two ITRs, one of which is preferably proximal (within about 250 bp, preferably within 100 bp, more preferably within 25 bp) to a phage packaging site. The replication-deficient eukaryotic viral genome is defined to be between the ITRs on the DNA segment comprising the eukaryotic viral packaging site. To support the replication of the eukaryotic viral vector carried by the lambdid vector, the lambdid vector also comprises DNA sequences that are not between the ITRs and that provide in trans the gene functions necessary for the replication of the viral vector that resides between the ITRs (and which is defined by the ITRs). The lambdid vector can be replicated in a bacterium and, if desired, encapsidated in a phage capsid comprising a chimeric coat protein (as described above). The chimeric coat protein mediates internalization of the encapsidated lambdid into the eukaryotic cell. While in the eukaryotic cell, the sequences outside the ITRs complement the replication deficiencies of the deficient viral genome. The eukaryotic viral vector produces its own coat and replication-deficient eukaryotic viral vectors are obtained. Significantly, this method can be designed such that there can be no homologous recombination event that would generate (contaminating) replication competent eukaryotic virus by ensuring that no overlapping sequences between the replication deficient eukaryotic viral vector and the complementing genetic elements exist. In this way a stock of replication-deficient eukaryotic virus can be prepared without the need of preparing a complementing cell line or using a helper virus. A lambdid vector illustrative of this embodiment is depicted in FIG. 5.

The present invention also provides a system for the generation of recombinant DNA vectors. Any embodiment of the present inventive vector can constitute a portion of the present inventive system. The present inventive system comprises at least a second DNA that comprises two DNA segments each of which have sufficient homology to the inventive vector to mediate homologous recombination and which flank or surround a DNA that is desirable to incorporate into the present inventive vector or into a portion of the eukaryotic viral DNA or amplicon that forms a portion of the present inventive vector. In embodiments comprising a deficient or conditionally deficient lambdoid origin of replication, the present inventive system can comprise a third DNA that can complement in trans the deficiency in a lambdoid origin of replication and, optionally, a fourth DNA that expresses a source of phage capsids that encapsidate intermediate or product vectors comprising the phage origin of replication. Either or both of the third and fourth DNAs of the inventive system can be optionally incorporated into the genome of a bacterial cell and/or can be comprised by one DNA.

The skilled artisan will appreciate that each of the foregoing embodiments of the present inventive vector enables certain embodiments of the present inventive method. The following descriptions will more fully illustrate the present inventive method.

According to the present invention, a DNA vector can be made and packaged by transfecting a bacterial cell with any embodiment of the present inventive vector and a second vector that has two DNA segments that are sufficiently homologous to the first vector to enable a double homologous recombination event between the vectors. Preferably, both the first and second vectors comprise at least one positive selection gene (which are preferably different), so that the cell can be grown under conditions that are selective for the maintenance of both vectors in the cell. After maintaining the transfected bacterial cell for a suitable time in culture, or on a plate, a double homologous recombination event produces a vector that has a phage packaging site and that does not contain the regulatable anti-selective gene of the present invention.

Of course, other vector moieties will be present in that cell as well. These other vector moieties comprise the original or starting vectors and the derivative of vector 2 which comprises the anti-selective gene. The present invention allows the facile removal or elimination of these undesired vectors.

First, only the product vector and the original vector contain phage packaging sites. Vectors that do not contain the phage packaging site can be eliminated by causing the packaging of the present inventive vector and the product vector while within the bacterial cell and infecting the phage into a second population of cells.

Any suitable technique for encapsidating these vectors into a phage capsid can be used. For example, the bacterial cell may contain a lysogen which can be activated. Alternatively, the bacterial cell can be superinfected with a helper phage. The helper phage can be either a wild type phage or can be deficient in an important phage gene function, e.g., it can lack a functional origin or replication or a phage packaging site.

The encapsidated product vector can be isolated from the first vector by appropriate design of the first vector. For example, the first vector can be made too large or too small to be effectively encapsidated into the phage capsid. The type of phage capsid, of course, is determined by the type of phage packaging site found on the first vector (e.g., if the first vector comprises a cos site, then the capsid will be a lambdoid, preferably a lambda capsid.

Alternatively, the encapsidated vectors (i.e., the first vector and the product vector) can be infected or transfected into a population of cells under conditions such that the regulatable anti-selective gene becomes active. The method is then finished by allowing the cells to grow (since cells comprising the first vector will be at a strong selective disadvantage or may die), and harvesting the product vector from a primary colony or a culture of the cells. The skilled artisan will recognize that the growth period is selected to avoid the appearance of variants. The variants typically will not begin to substantially contaminate the culture or plate for at least about 24 hours after induction of the NSG. Of course, the method can also comprise a screening or sequencing step, if desired.

The skilled artisan will readily appreciate how to induce the anti-selective gene. For example, if the NSG is a constitutively expressed sacB gene, the NSG can be activated by supplying sucrose to the medium allowing leaven to be produced. A plethora of other embodiments are well known in the art. If an NSG is regulated by a small chemical inducer, e.g., Tac-ccdB gene, it can be activated by adding the inducer (e.g., IPTG) to the growth medium. If the anti-selective gene is the T7 promoter linked to an NP-1 gene, this NSG can be activated simply by infecting a cell that expresses T7 RNA polymerase. Similarly, if the anti-selective gene is an SRG, e.g., the EM-7 promoter linked to a zeocin gene, the SRG can be activated simply by infecting a cell that expresses T7 RNA polymerase. Advantageously, when the EM-7 promoter is linked to a DNA encoding a positive selection protein, the SRG can serve two functions. In the first bacterial cell the constitutive promoter of the EM-7 gene will provide constitutive production of the positive selection protein. However, when the same gene is in a cell containing a suitable level of T7 RNA polymerase, this otherwise positive selection gene becomes a strong anti-selective gene.

A preferred embodiment of the present invention which has been found to function as well as any other embodiment and better than a few embodiments comprises a first (inventive) vector that comprises a PSG that is either proximal or adjacent to an NSG and an independent positive selection gene. In this embodiment the PSG is a zeocin resistance gene and the independent positive selection gene is a kanamycin resistance gene, or yet more preferably, a tetracycline resistance gene. Additionally, in this embodiment of the present invention the inventive vector preferably comprises a pBR322 origin of replication.

In a further embodiment of the present invention, the first bacterial cell (into which the first and second vectors are transfected) is competent for homologous recombination, but the second population of cells into which the encapsidated products are infected (or transfected) is deficient in the ability to support homologous recombination. This phenotype can be obtained by a multiplicity of suitable mechanisms. One type of cell that is deficient in the ability to support homologous recombination is any cell deficient in recA. A multiplicity of recA deficient strains are publicly available.

Another embodiment of the present invention employs a first vector that comprises a lambdoid origin of replication. It is strongly preferred that the lambdoid origin of replication be defective or conditionally defective, and that the defect can be complemented in trans or otherwise mitigated by manipulation of the cellular environment. As in other embodiments of the present inventive method, the first and second vector are transfected into a bacterial cell. However, in the present embodiment, the double homologous recombination event is facilitated by infecting (or transfecting) the cell with a defective or non-defective helper phage or by activating a defective or non-defective lysogen. The helper phage or lysogen complements the defective lambdoid origin in trans. As a result, the first vector begins lambdoid replication, which provides higher copy numbers of the first vector and substantially enhances the rate of homologous recombination. The helper function can be provided by lambda clear. The helper function can also be provided by a vector with a packaging site that can be disabled or deleted. For example, the packaging site of the helper can be flanked by site-directed homologous recombination sites (e.g., lox sites). Accordingly, if the first and second vector are initially transfected into a cell expressing a suitable recombinase (e.g., cre), when the helper phage is infected into the cell it will be not be capable of being packaged into capsids and cannot interfere with later steps of the inventive method. Even if the helper phage is encapsidated and carried to the next step of the inventive method, the helper vector can be eliminated by placing the second population of cells under conditions selective for the product vector and anti-selective for the helper phage. The skilled artisan will readily appreciate that additional permutations and combinations of the present invention can also be used.

EXAMPLES

The following examples further illustrate the present invention but should not be construed to be limiting in any way. Although the examples are illustrated with lambda vectors and adenovirus, the skilled artisan will appreciate that the following examples can be applied to other lambdoid vectors and to non-adenoviral eukaryotic viruses.

Example 1

The following example illustrates LOI$^Q$VXB(Spe), a vector useful in the context of the present invention.

The LQI$^Q$VXB(Spe) vector comprises a lambda operon $P_R$ that drives transcription through gene O. In this particular vector, Cro and CII comprise deletion mutations in essential regions of their coding sequences, thereby eliminating the Cro and CII gene functions. For example, Cro is deleted of amino acids 15–38 (i.e., α helices 2 and 3), and CII is deleted of amino acids 6–20. Protein O is still expressed.

The vector also comprises a Lac I$^Q$ operon. Downstream of the Lac I$^Q$ promoter and gene is a cos site. The orientation of the cos sites with respect to the $P_R$ promoter is the same as the orientation of the cos site with respect to $P_R$ found in wild-type lambda. Each of the aforementioned genetic elements are contained on one DNA segment comprising a Pac I site at each terminus. The vector further comprises a kanamycin resistance gene and the p15 origin of replication from pACYC177 (New England BioLabs).

A first transgene expression cassette (e.g., a CMV promoter operably linked to DNA encoding the bacterial Lac Z gene, or alternatively human $VEGF_{121}$cDNA, and an SV40 polyadenylation sequence) is adjacent to the Ad5 position 1–355 segment. Continuing from the transgene expression cassette is a DNA segment comprising Ad5 sequences from positions 27,082 to 32,852 which have sequences from 27,860 to 30,805 deleted and which are obtained from Xba I digestion of Ad5. The Spe I site in this vector is unique. The E. coli β-glucuronidase gene and SV40 early polyadenylation signal are placed next to the Ad5 sequence terminating at position 32,852 and in the same orientation as the aforementioned transgene. A DNA segment corresponding to Ad5 from position 35,565 to position 35,935 resides next to the β-glucuronidase coding sequence. This places the β-glucuronidase gene under control of the Ad5 E4 promoter.

Example 2

This example illustrates useful modifications of $LOI^QVXB(Spe)$.

Figure 2:
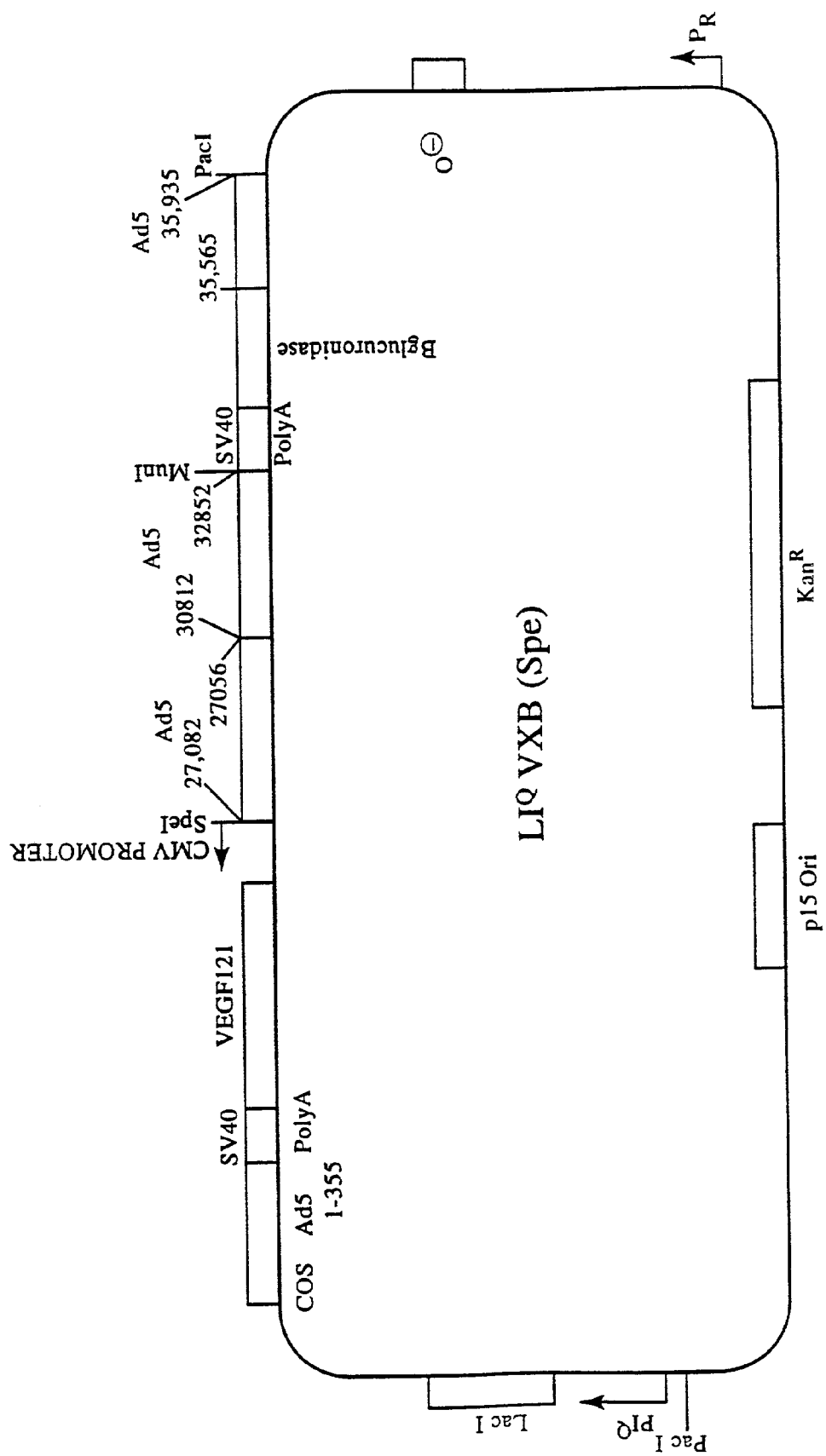
FIG. 2 depicts the lambdid vector $LI^Q VXB(Spe)$.

$LOI^QVXB(SpeCC)$ shown in FIG. 1 is made by a deletion spanning the coding sequences from the Cro gene through the CII gene of $LOI^QZXB(Spe)$. A deletion to the O gene of $LOI^QZXB(Spe)$ produces $LI^QZXB(Spe)$ shown in FIG. 2. A deficiency in the O gene can be made by cutting it with Bgl II and re-ligating the O gene which results in the loss of a small essential fragment of the O gene without disrupting the lambdoid origin of replication. The deletion of Cro through CII is approximately lambda coordinates 38,041 to 38,653. This also removes $tR_1$.

Example 3

This example demonstrates the production of lambdid vectors comprising all of an adenoviral genome except for portions of the E1, E3, and E4 regions.

Figure 3:
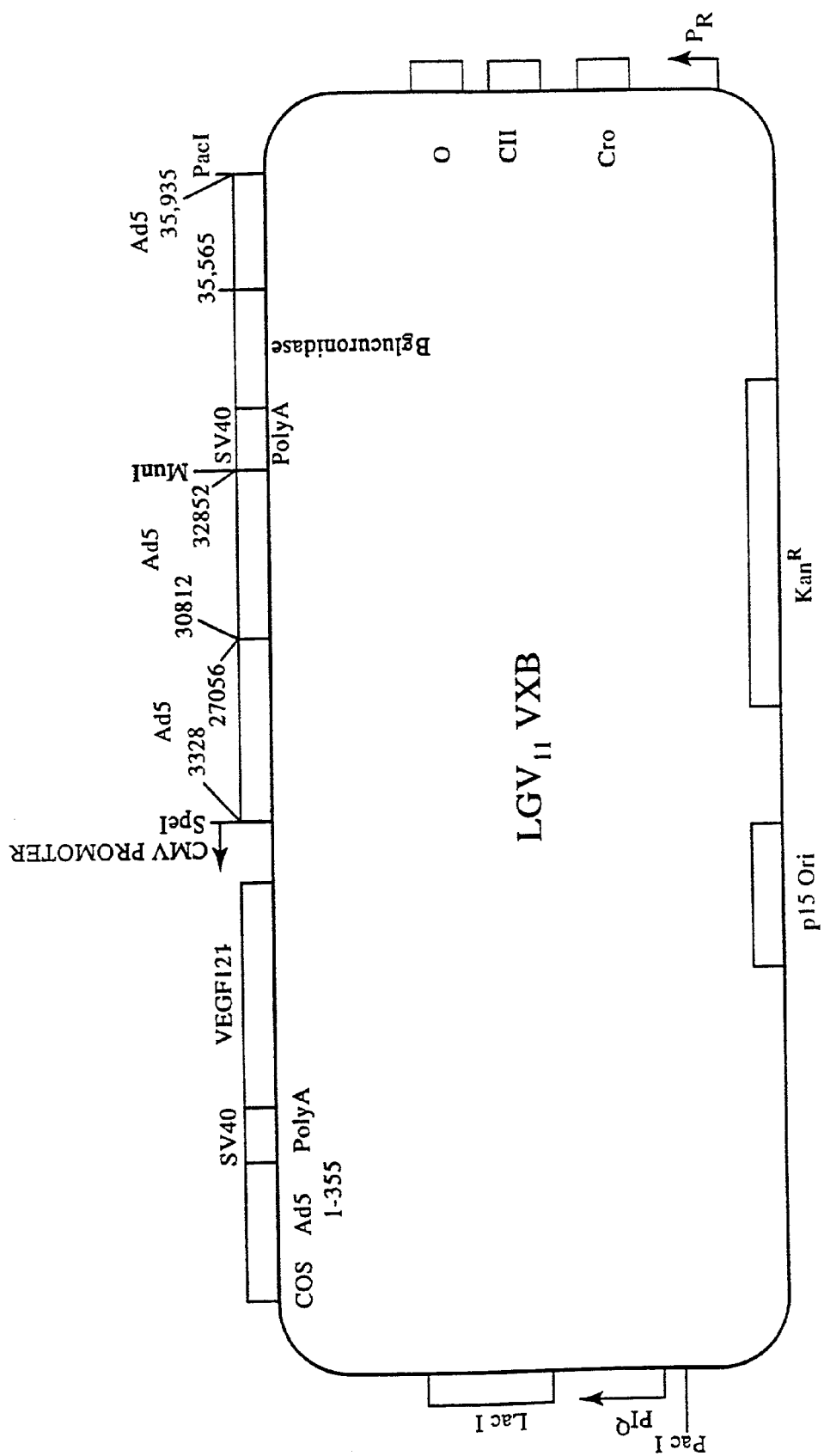
FIG. 3 depicts the lambdid vector $LGV_{11}VXB$.

An Ad5 virus containing an Spe I site at position 3,328 of the wild-type genome was generated by standard virus construction techniques. Digestion with Spe I yielded an expected fragment of about 23.7 kbp which was isolated. The isolated fragment was inserted into $LOI^QVXB(Spe)$ to generate the lambdid vector $LGV_{11}VXB$ which is shown in FIG. 3. By an anlagous process, each of the vectors of Examples 1–3 and the like can be used to generate a lambdid vector containing an adenovirus.

The lambdid vector can be amplified and digested with Pac I, and the Pac I segment containing the adenoviral sequences can be transferred to a eukaryotic cell capable of supporting the growth of the recombinant adenovirus. In the present example, 293/ORF6 cells (see International Patent Application WO 95/34671, Kovesdi et al.) would be suitable cells, because they complement the deficiencies in the essential gene functions deleted from the E1 and E4 regions of the adenoviral genome. The adenoviral stock produced in this manner is free of replication competent adenovirus and wild-type adenovirus since none of these are packaged into the lambdoid phage.

Alternatively, a bacterial cell comprising $LGV_{11}VXB$ can be infected with a helper phage (or a lysogen it contains can be activated). The presence of helper phage functions results in the linearization of $LGV_{11}VXB$ at the cos site and the encapsidation of the linearized vector. As can be seen by inspection, linearization results at the cos site generates an ITR near one terminus of the DNA. Therefore, the encapsidated, linearized vector can be transduced into a permissive eukaryotic cell (e.g., 293/ORF6 cells), which in turn is followed by unencapsidation of the vector, and propagation of the eukaryotic viral gene transfer vector (i.e., the adenoviral vector).

Example 4

The construction of an adenovirus by using viral arms is a time consuming process. If multiple regions of the genome need to be altered, either sequential virus construction processes are employed or partially complementary arms from different recombinant viruses are required. Often suitable restriction sites are not readily available. Further, a negative selection pressure can exist with respect to the desired adenovirus in a eukaryotic cell, which can further hinder attempts to obtain the desired vector. This example demonstrates a suitable solution to a long felt need and demonstrates the increased rate and ease of generation of various adenoviral vectors that can result from the use of the present inventive lambdid vectors and system.

Figure 4:
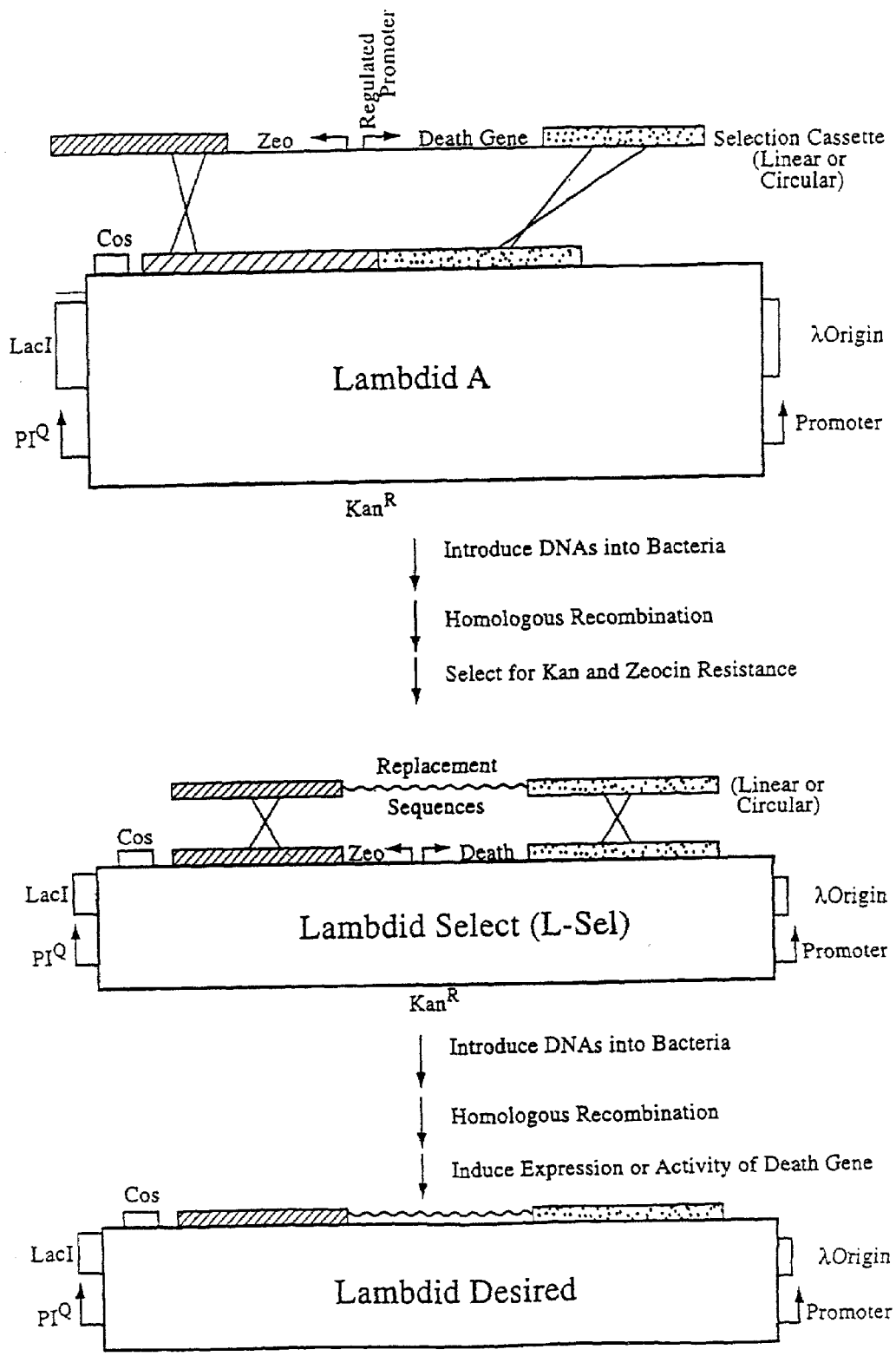
FIG. 4 depicts the structure of several DNA vectors useful in the context of the present invention, particularly L-sel.

As disclosed above, replacement of a desired region of a lambdid vector is facilitated by positive and/or negative selection. Preferably, both positive and negative selection are used together for optimum ease of vector construction. FIG. 4 depicts a process wherein two homologous recombination steps are used to generate a final lambdid vector.

First, a cassette is introduced into the region to be modified by homologous recombination. The cassette contains a positive and negative selection gene and preferably introduces a unique restriction site. The negative selection gene is placed under the control of a regulatable promoter or can be placed under the control of a constitutive promoter when the negative selection gene product catalyzes the conversion of a non-toxic substance (which can be provided or withheld) into a lethal metabolite. The intermediate lambdid vector thereby produced is called Lambdid select (L-sel). L-sel contains genes for both tetracycline and zeocin resistance whereas neither precursor vector confers resistance to both antibiotics to a bacterium containing only one of the vectors.

A third vector, comprising sequences to be introduced into the L-sel vector and homologous to L-sel at two distinct loci which flank the negative selection ("death") gene, is transduced into a bacterial cell comprising L-sel. L-sel and the third vector recombine. The recombination event excises the negative selection gene from L-sel at the same time that the desired sequence is introduced. The reaction gives rise to a population of vectors in which the desired product is underrepresented. Therefore, the desired (final) lambdid vector ("lambdid desired") is enriched by activation (e.g., provision of a substrate) or induction of the negative selection gene. Bacteria comprising undesired reactants and products do not propagate. The desired product is, therefore, easily identified with routine screening.

Ampicillin, kanamycin, zeocin, and geneticin (G418) are illustrative of positive selection antibiotics useful in the context of this example. A Tac (Trp and Lac hybrid) promoter which is repressible by Lac I operably linked to a DNA encoding OmpA FLAG/NP-1 fusion protein is illustrative of a negative selection gene useful in the context of this example. OmpA FLAG/NP-1 is a rat defensin lacking its cognate signal sequence. The Tac promoter is inducible by IPTG.

The unique restriction site introduced into L-sel by the selection cassette is useful (but optional) in at least two respects. Linearized DNA with free ends have increased rates of homologous recombination. Combining linearized L-sel with the target DNA will yield higher rates of recombination. The unique restriction site is also of use when the recombination event occurs (this event dimerizes the vectors) between intact circular DNAs when a single, rather than multiple, recombination event occurs. In that case, the recombinant vectors can be digested with the unique restriction enzyme. Advantageously, the unique restriction enzyme can be expressed from an inducible gene in vivo, which provides continuous cutting of the moieties comprising the unique restriction enzyme site and prevents the need to isolate the DNA for restriction digestion. All of the non-recombinant and singly recombined vectors will be linearized. The linearized DNAs are selected against when transferred into bacteria since they do not stably transform bacteria. The non L-sel vector can be selected against by antibiotic selection. In contrast, the dimerized vector can undergo a second round of homologous recombination to generated the desired product. The vector population can be purified from the bacteria, digested at the unique restriction site, and re-transduced into a bacteria to enrich the vector population for the desired product. The requirement for restriction can be avoided with the negative selection cassette in L-sel vectors, by inducing the expression of the "death" gene in all non recombined L-sel vectors.

Example 5

This example demonstrates the generation of adenovirus from a lambdid vector.

The lambdid vector $LGV_{11}VXB$ (FIG. 3) is amplified in a bacterial host and isolated. The vector is digested with Pac I, which produces a DNA segment that contains at least one fragment that is highly homologous to an adenoviral sequence. The DNA fragment comprising the DNA segment highly homologous to an adenoviral sequence is transferred into a eukaryotic cell culture permissive for the growth of that adenovirus (e.g., 293/ORF6 cells). After multiple passages, cytopathic effect is observed.

Example 6

This example demonstrates the production of recombinant D protein comprising a sequence that targets the protein or a phage capsid comprising the protein to the surface of a eukaryotic cell, thereby effecting its uptake into endosomes of the eukaryotic cell.

A plasmid comprising the DNA encoding the D gene operably linked to the Tac promoter, pD100, is prepared by conventional techniques. Standard site directed mutagenesis is used to introduce a DNA encoding either the amino acid sequence (a)Gly Ser Gly Ser Gly Ser Gly Ser Gly Ser Ala Cys Asp Cys Arg Gly Asp Cys Phe Cys Gly [SEQ ID NO: 2] or (b) Gly Ser Gly Ser Gly Ser Gly Ser Gly Ser Lys Lys Lys Lys Lys Lys Lys [SEQ ID NO: 3] into the coding sequence of D. The added amino acid sequence is placed at the carboxy terminus of the D protein but also can be placed at the amino terminus of the D protein. By including the sequence of SEQ ID NO: 2, the D protein will specifically bind to any cell that expresses the αvβ3 integrin on its surface. By including the sequence of SEQ ID NO: 3, the D protein will bind to a cell having heparin sulfate on the surface.

The recombinant D protein is overexpressed in bacteria and isolated by conventional means. During the isolation of the recombinant D protein, the bacterial culture is separated by differential centrifugation to separate inclusion bodies, if any, from soluble material. The extent of soluble D protein will depend on the particular placement of the added amino acid sequence. At least 20% of the protein partitions to the supernatant, thus demonstrating proper folding of the D protein. The affinity of the D protein for eukaryotic cells can be confirmed using any suitable assay, including direct binding measurements and inhibition assays.

Example 7

This example illustrates the use of a modified T7 vector for gene transfer to eukaryotic cells.

The expression cassette CMV-GFP is positioned immediately 3' of gene 10 in the genome of T7 so that it is transcribed leftward (with respect to the linear T7 genome). The expression cassette CMV-GFP consists essentially of the CMV immediate early promoter, a coding sequence for the Green Fluorescence Protein (Gibco BRL Life Technologies), and the SV40 early polyadenylation signal. The T7 gene 10 promoter region is deleted from the phage genome, resulting in very low levels of its expression. However, a modified gene 10 product (i.e., modified p10) is provided by a plasmid in trans. Its expression is regulated by the gene 10 promoter so that it is overexpressed. Amino acid 344, the last amino acid of p10A, is changed to valine, and the stop codon is changed to glutamic acid before addition of a constrained RGD sequence. The 3' terminal coding sequence and carboxyl terminal amino acid sequence of the modified gene 10 product are, e.g.,

```
GTG GAA GAG ATC TAT AGC GGT AGC GGC AGC GGT AGC GCG TGC GAT TGT CGT GGT  [SEQ ID NO:4]
Val Glu Glu Ile Tyr Ser Gly Ser Gly Ser Gly Ser Ala Cys Asp Cys Arg Gly  [SEQ ID NO:5]

GAT TGC TTC TGC GGC
Asp Cys Phe Cys Gly
```

When this recombinant T7 phage is contacted to eukaryotic cells comprising the αv integrin and treated with chloroquine, GFP activity can be detected in the cells 24–48 hours later.

Example 8

This example illustrates a straightforward method of using a lambdid vector to generate a product-vector, such as a recombinant eukaryotic viral vector, suitable for use in gene transfer to eukaryotic cells. The product-vectors generated by the present method comprise a eukaryotic viral amplicon. This example teaches and illustrates a general method. However, the example also includes a specific embodiment to aid understanding of this method.

Figure 7:
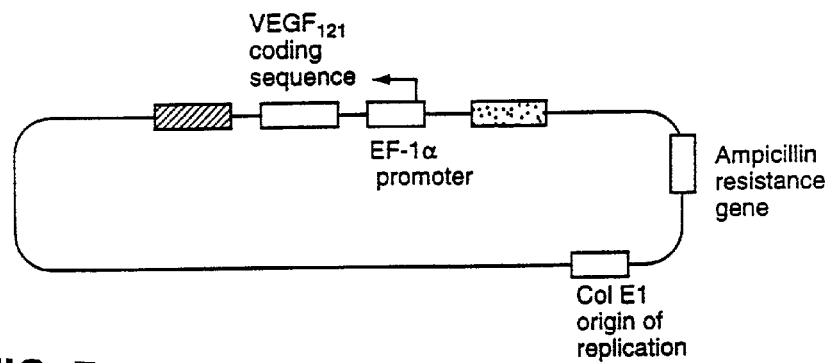
FIG. 7 depicts one embodiment of Vector 8. Vector 8 can be used in combination with Vector 7 (see Example 8 below).

This method utilizes a lambdid vector, Vector 7, and another DNA, Vector 8. One embodiment of Vector 7 is depicted in FIG. 6. One embodiment of Vector 8 is depicted in FIG. 7.

Vector 7

Vector 7 comprises a eukaryotic viral amplicon, a eukaryotic viral vector, or sequences highly homologous to a eukaryotic viral vector (i.e., a eukaryotic viral DNA). Because this method preferably generates product-vectors comprising at least the genetic elements that are necessary and sufficient to form a eukaryotic viral amplicon, the eukaryotic viral DNA carried by Vector 7 also preferably comprises the elements required to make an amplicon. However, one or more elements of an amplicon can be transferred to Vector 7 by homologous recombination with Vector 8 or another suitable DNA. The particular embodiment of Vector 7 depicted in FIG. 6 carries an adenoviral vector, which is deficient in the E1 and E4 regions of the adenoviral genome. FIG. 6 also depicts two terminal ITRs and an adenoviral packaging site, because these three genetic elements are necessary and sufficient to form an adenoviral amplicon.

Vector 7 can (and usually does) comprise additional sequences of a eukaryotic viral vector. The particular embodiment of Vector 7 illustrated in FIG. 6 comprises a complete wild-type adenovirus with the exception that most of the E1 region (Ad5 coordinates 356 to 3,327) and the E4 region (Ad5 coordinates 32,832 to 35,564) are replaced by heterologous genetic elements.

The purpose of Vector 7 (in this example) is to facilitate homologous recombination into one region of the eukaryotic viral DNA that it carries. In the particular embodiment illustrated here, the E1 region of the adenoviral vector comprises either a highly-regulatable negative selection gene (NSG), or a dual selection cassette (DSC), which is inserted into, or in place of, a region of the eukaryotic viral DNA. The substitution of the NSG, or DSC (which by definition comprises an NSG), for the E1 region in FIG. 6 dictates that the E1 region or a region comprising the E1 region will be replaced by homologous recombination with Vector 8 in this method. It is preferred (but not essential) that Vector 7 comprises a DSC, rather than a NSG. After homologous recombination, the NSG will be activated to select against bacteria comprising the NSG.

In the initial steps of the procedure, the bacteria transduced with Vectors 7 and 8 are grown under conditions that select for bacteria harboring either Vector 7, or Vectors 7 and 8. Vector 7 has an independent positive selection gene (kanamycin resistance in the present embodiment) and selective pressure for Vector 7 can be obtained by adding kanamycin to the growth medium. However, selective pressure for Vector 7 also can be obtained by utilizing the positive selection gene of the DSC (zeocin resistance in the illustrated embodiment). Selection for the PSG of the DSC is advantageous because the PSG and the NSG resident in the DSC are (in terms of genetics) more tightly linked because of their physical proximity to each other than are the NSG and the independent positive selection gene. To obtain the highest degree of efficiency in obtaining the desired vectors in the present method, so-called "background" propagation of undesired vectors is preferably limited to the greatest extent possible. Therefore, the use of the positive selection gene of the DSC to maintain pressure for Vector 7 is preferred to the use of the independent positive selection gene in the initial stages of this method. The skilled artisan will, of course, recognize that the growth medium could be formulated to be selective for both positive selection genes of Vector 7 (e.g., in the illustrated embodiment, formulated to contain both zeocin and kanamycin).

The eukaryotic viral vector carried by Vector 7 can have other modifications in addition to the insertion of a DSC or negative selection gene into or in place of a region of the eukaryotic viral vector. The illustrated embodiment of the present method teaches this by showing that the E4 region of the adenoviral vector is replaced by a Transcriptionally Inert Spacer (TIS). However, it will be appreciated that many other modifications can be made to the eukaryotic viral vector. The depicted TIS is an SV40 polyadenylation sequence, followed by a bacterial β-glucuronidase coding sequence, followed by a human β-globin polyadenylation sequence. The TIS element is incorporated to improve the characteristics of the adenoviral vector produced in the present example. TIS elements are more thoroughly described in International Patent Application WO 97/21826.

An important feature of Vector 7 is that it contains two DNA segments (homology regions) that are highly homologous to two DNA segments (homology regions) of Vector 8. These homology regions of Vectors 7 and 8 are used to mediate homologous recombination between the two vectors. In the particular embodiment illustrated herein, the adenoviral sequences from coordinate 1 to 355 and from coordinate 3328 to at least about 5,678 are present in both Vector 7 and Vector 8 and are depicted in each figure as striped and stippled boxes to indicate their identity.

Vector 7 also has a packaging site providing for encapsidation into a lambdoid capsid (e.g., a lambda cos site). The lambdoid encapsidation site is preferably proximal to an ITR of the eukaryotic viral DNA so that that the ITR will become proximal to a (free) terminus of the DNA following the linearization of the lambdid vector that occurs during encapsidation into a lambdoid capsid.

The Vector 7 depicted in FIG. 6 also comprises a $LacI^Q$ gene, a low copy number, bacterial origin of replication, and an independent positive selection gene.

The $LacI^Q$ gene of the Vector 7 depicted in FIG. 6 is optional. In the depicted embodiment, it allows for the tight regulation of the Tac promoter that governs the depicted $NSG$ (in this case the NSG forms part of the DSC). The $LacI^Q$ gene overexpresses the lac repressor, which effectively silences the Tac promoter in the absence of galactose or a galactose analog (e.g., IPTG). If a promoter other than the Tac promoter is used to drive the expression of the NSG, if a $LacI^Q$ strain is used, or if other highly effective means of controlling the negative selection pressure of the NSG are employed, then the $LacI^Q$ gene can be deleted from Vector 7 without effect.

The low copy number origin of replication serves to stably maintain Vector 7 in the bacterial cell when the lambdoid origin is inoperable. The vector depicted in FIG. 6 comprises more than 38 kbp. Accordingly, it is advantageous to incorporate a low copy number origin of replication, such as the p15 Ori (as shown in FIG. 6) or as the pBR322 ori (not shown). While not wishing to be bound to any particular theory, it is believed that low copy number origins of replication help to maintain the integrity of large, autonomously-replicating DNAs, such as large lambdid vectors.

Figure 8:
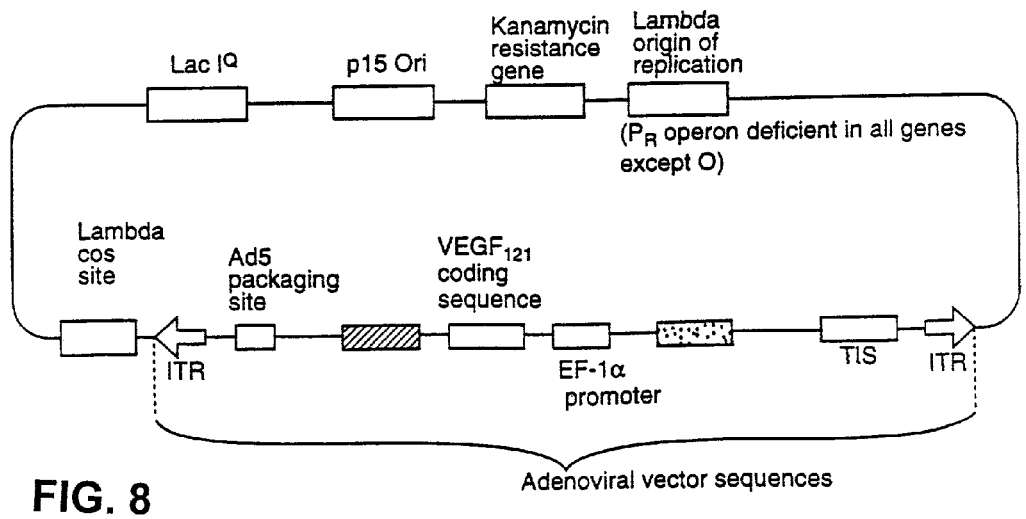
FIG. 8 depicts an embodiment of Vector 9. Vector 9 is one of the desirable products that can be obtained by homologous recombination between Vector 7 and Vector 8.

The independent positive selection gene does not reside within the dual selection cassette, nor within any region of the lambdid vector intended to participate in the homologous recombination reaction with Vector 8. Therefore, the independent positive selection gene of Vector 7 will become part of the desired product-vector, Vector 9 (FIG. 8).

Figure 9A:
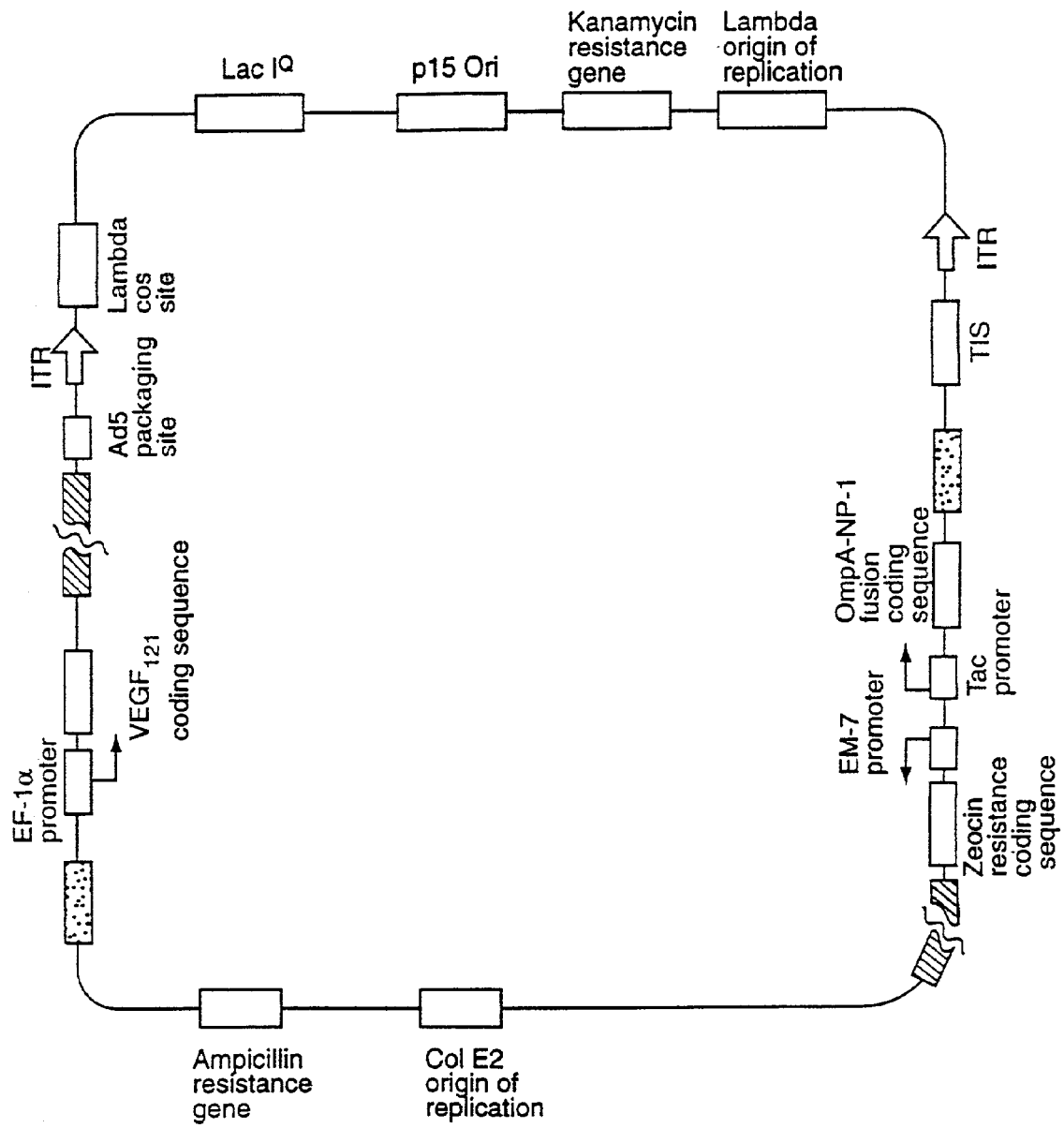
FIG. 9A depicts one of the by-products of homologous recombination between Vector 7 and Vector 8.
Figure 9B:
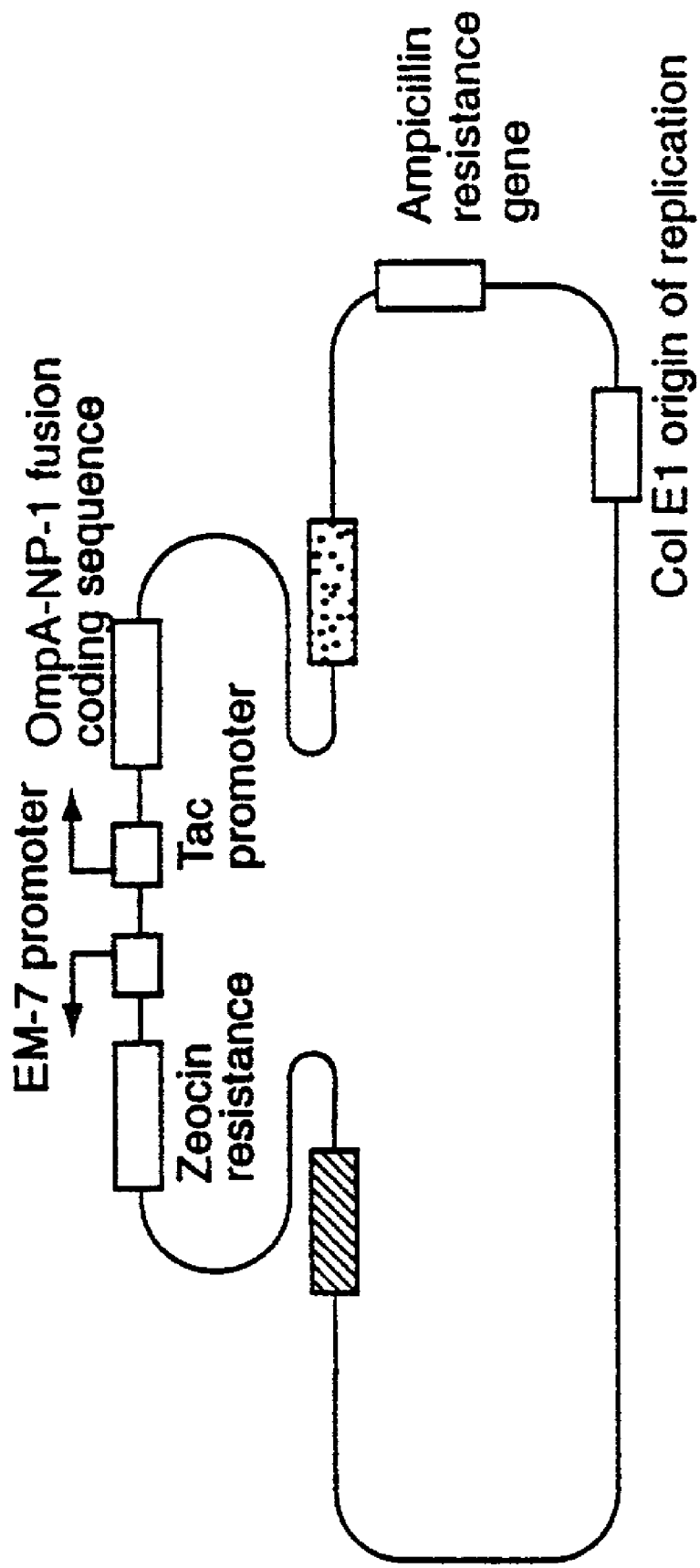
FIG. 9B depicts yet another one of the by-products of homologous recombination between Vector 7 and Vector 8. Example 8 illustrates a useful method for making and isolating Vector 9 from Vectors 7 and 8 and the vectors depicted in FIGS. 9A and 9B.

Following homologous recombination between Vectors 7 and 8, the vectors depicted in FIGS. 9 and 10A–B will be produced. The vector of FIG. 8 comprises the desired adenoviral vector, but will not comprise the positive selection gene of the dual selection cassette (which resides within the adenoviral vector sequences in FIG. 6). In order to select for bacterial cells comprising the vector depicted in FIG. 8, the cells are grown in or on medium selective for cells comprising the independent positive selection gene (derived from Vector 7). The independent positive selection gene shown in FIG. 6 is a kanamycin gene. In contrast, the medium is not selective for the PSG of the DSC since this selection gene now resides only on undesired products. Accordingly, all transformed bacterial cells in this particular example are grown in the presence of kanamycin, but not zeocin at this point in the procedure.

Vector 7 also comprises a lambda origin of replication. The lambda origin of replication comprises at least two gene functions: a site to assemble the replication proteins and a promoter that drives transcription through these sequences. The lambda origin depicted comprises the $P_R$ operon which has been rendered deficient in at least O or P. This is advantageous, inter alia, to prevent run-away replication of Vector 7.

Vector 8

The vector depicted in FIG. 7 comprises two non-adjacent segments that are highly homologous to sequences in the adenoviral vector comprised by Vector 7. Between these two non-adjacent sequences is an expression cassette comprising a DNA encoding a protein of interest, and, operably linked thereto, a promoter that functions in at least some eukaryotic cells (e.g., a target cell of the adenoviral vector comprised by Vector 7 or Vector 9). In the depicted embodiment, Vector 8 comprises an EF-1α promoter (Uetsiki et al., *J. Biol. Chem.*, 264, 5791–5798 (1989)) operably linked to a $VEGF_{121}$ coding sequence, forming a synthetic $VEGF_{121}$ gene. The $VEGF_{121}$ gene is flanked by regions having high homology to adenoviral sequences in the embodiment of Vector 7 depicted in FIG. 6.

Vector 8 also comprises an optional positive selection gene (e.g., an ampicillin resistance gene), which is preferably a different gene than the positive selection gene of the dual selection cassette and the independent positive selection gene of Vector 7. Vector 8 preferably does not comprise a phage packaging site that is compatible with the phage packaging site of Vector 7. That is, in the event that Vector 8 comprises a phage packaging site, that phage packaging site will be selected such that it does not direct the encapsidation of Vector 8 into a capsid capable of encapsidating Vector 7. Alternatively, Vector 8 can be designed to be too large or too small for efficient encapsidation or can have another suitable impediment to encapsidation. Optionally, Vector 8 can additionally comprise a lambdoid origin of replication.

Figure 10:
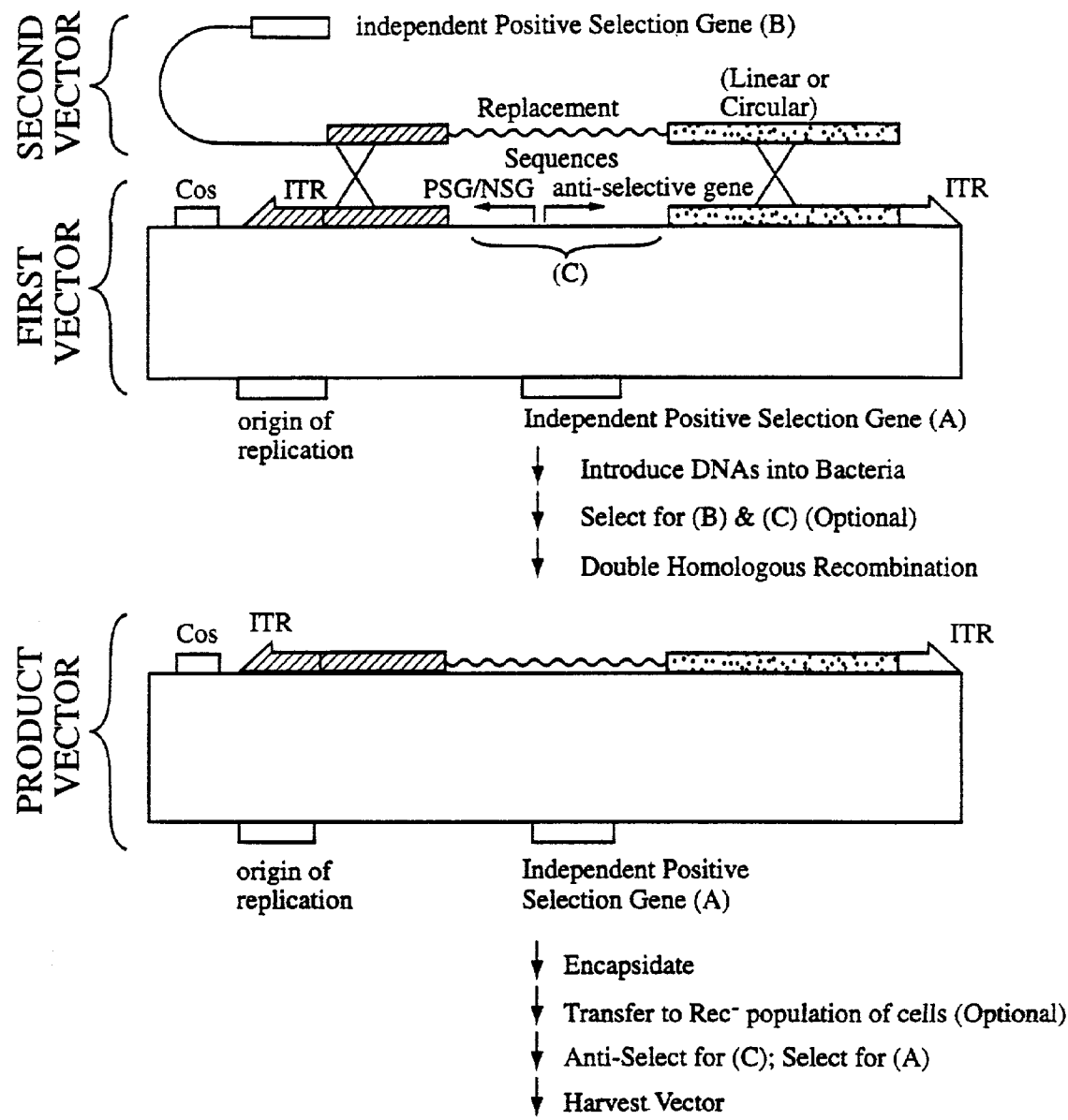
FIG. 10 depicts a preferred embodiment of the present invention.
Figure 11:
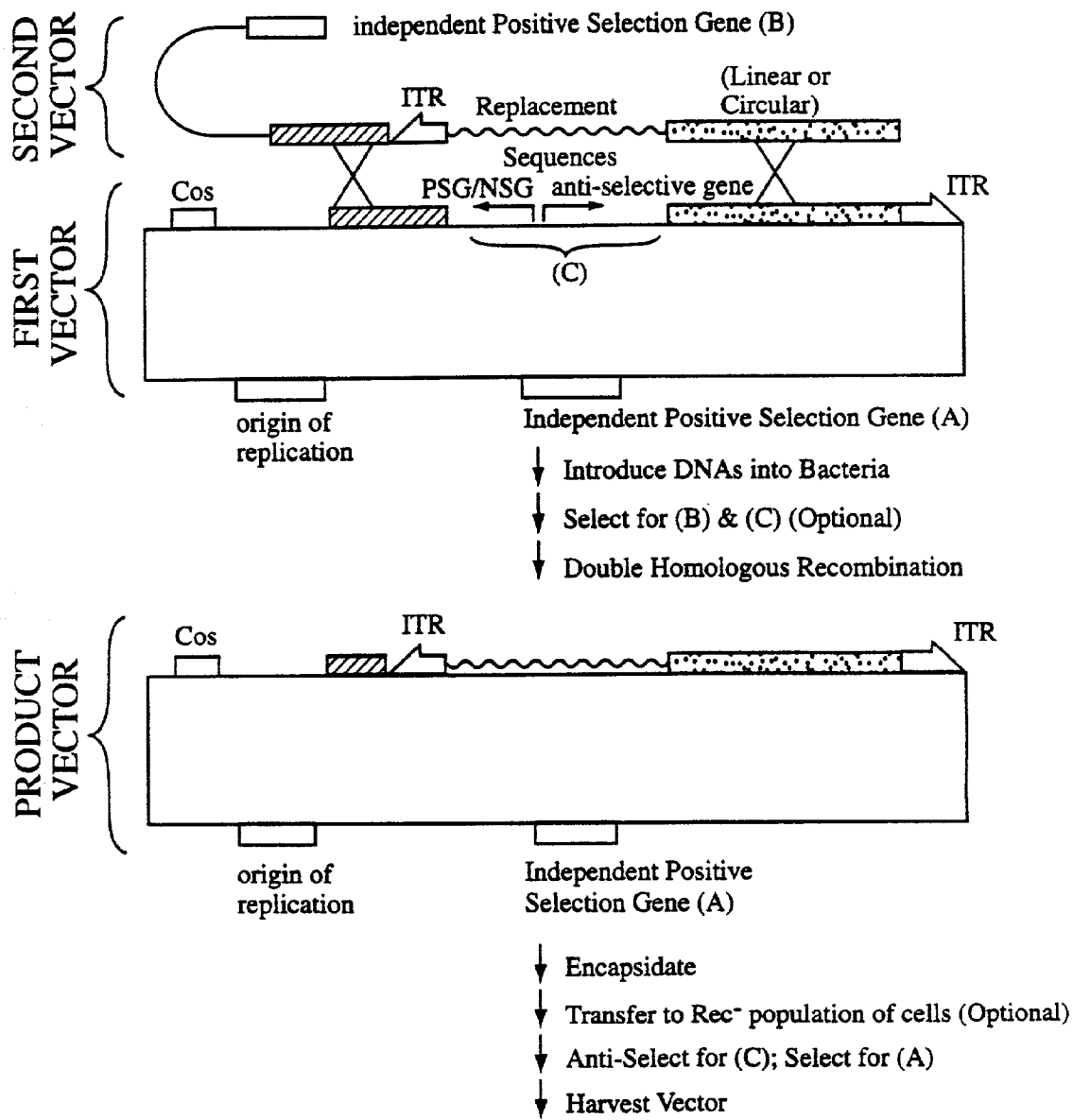
FIG. 11 depicts a preferred embodiment of the present invention. The embodiment of the present invention depicted in FIG. 11 is nearly identical to the embodiment depicted in FIG. 10, except that in FIG. 11 one ITR of a eukaryotic viral genome is resident in the first vector and another ITR of a eukaryotic genome is resident in a second vector and the double homologous recombination transfers the ITR of the second vector to the product vector to form a eukaryotic viral amplicon.

The vectors of FIGS. 7 and 8 (i.e., Vectors 7 and 8) having been transformed into a single bacterial host can homologously recombine (through a double crossover) to generate the vectors depicted in FIGS. 9 and 10A–B. The vector depicted in FIG. 8 is the desired product. Both vectors depicted in FIGS. 7 and 8 are closed circular DNAs. This fact decreases the efficiency of homologous recombination, which is a phenomenon that occurs at a low frequency, even under optimum conditions. Additionally, the vector depicted in FIG. 8 will be found in a minority of bacterial cells growing in a culture. Other cells growing in the same culture will contain one of more of the vectors depicted in FIGS. 7, 8, and 10–B. The culture of bacterial cells also will comprise a vector produced by a single crossover event between the vectors of FIGS. 7 and 8. The product of a single crossover by homologous recombination (a vector dimer or supervector) will comprise all the nucleotides of the vectors of both FIGS. 7 and 8. If a second homologous recombination event could be encouraged, this supervector would give rise to either the vectors of FIGS. 7 and 8, or to the vectors of FIG. 8 and 10–B. These impediments are suitably overcome by infection of the population of transduced cells (comprising Vectors 7, 8, 9, and Vectors 10–B) with a helper phage (e.g., lambda clear) or by activating a (helper) lysogen within the cell.

The helper phage or lysogen is preferably conditionally defective such that its presence allows for the lambdoid replication and encapsidation of the lambdid vector, but does not itself become packaged. Such a helper phage or lysogen can be obtained by elimination of the packaging site or other suitable mechanism as is discussed elsewhere. If a defective helper phage or defective helper lysogen is employed, then the propagation of the helper can be prevented and separation of the helper phage and Vector 9 is easily achieved. Example 9 is directed to conditionally defective helper phage and lysogens. However, to more clearly illustrate the present invention the remainder of the present example assumes that the helper phage or lysogen is not defective.

Super-Transduction by Helper Phage or Activation of a Lysogen

The helper phage or activated lysogen, when present in a bacterial cell comprising the vectors depicted in FIGS. 7 and 8, causes the lambda origin resident on Vector 7 to mediate lambdoid replication. Lambdoid replication is well-known to enhance the rate of homologous recombination.

Additionally, the helper phage or activated lysogen provides all the gene functions necessary to replicate itself (unless a defective phage or lysogen is used) and any lambdid vectors contained in the same cell. As a consequence, vectors of appropriate size (i.e., a size between about 73% and about 110% of the wild-type phage genome) that comprise a phage packaging site (e.g., a lambda cos site) are packaged into phage capsids.

The vector depicted in FIG. 7, and vectors derived from the backbone of Vector 8, lack a compatible phage packaging site (i.e., in the present example, a cos site). The vectors of FIGS. 7 and 9, however, do comprise a suitable packaging site and lambda origin of replication. They are also designed to be roughly the same size as the wild-type helper phage (i.e., between 73% and 110% of the lambda genome). Thus, the helper phage directs the encapsidation of the vectors of FIGS. 7 and 9 into (lambda) capsids. Any supervectors within the cell also may be packaged providing that they are not larger than the upper size limit (of about 110% of a wild-type genome) for packaging into a capsid.

The present method continues by obtaining a phage-like lysate (i.e., a lysate of encapsidated lambdid vectors and possibly helper phage) and infecting a culture of suitable bacteria with the lysate. These infected cells will primarily comprise (1) helper phage, (2) Vector 7, and (3) Vector 9. The infected bacteria are grown under conditions that (1) are selective for the desired product-vector ("Vector 9") and (2) activate the negative selection gene (i.e., conditions that are anti-selective for Vector 7 and undesired product-vectors). Since the helper phage lacks the independent PSG (e.g., the Kan resistance gene), it is anti-selected. Moreover, the cell is preferably lysogenic, which prevents propagation of the helper phage or lysogen. The desired product-vector, which is Vector 9, is therefore efficiently separated from those products that are not efficiently encapsidated.

These bacteria comprising a mixed population of reactant and product vectors are clonally isolated, sub-cultured, screened to ascertain their identity, and propagated to provide a recombinant lambdid vector comprising a desired eukaryotic viral vector (pDesired).

The pDesired vector can then be utilized as recited in a variety of ways. For example, the pDesired vector is prepared for transduction into a eukaryotic cell. Preparation for transduction into a eukaryotic cell can comprise packaging (e.g., by means of a helper phage) into a phage capsid. Alternatively, preparation for induction into a eukaryotic cell can comprise linearization near an ITR of the eukaryotic viral vector (but not within the viral vector). The recombinant lambdid, having been prepared for transduction into a eukaryotic cell, is then transduced into a eukaryotic cell that is permissive for the replication of the eukaryotic viral vector. The eukaryotic cell is cultured and the eukaryotic viral vector is obtained by a modified Hirt procedure or any other suitable procedures.

Example 9

This example illustrates how to make and use a defective helper phage or defective helper lysogen in the context of Example 8.

In Example 8, a phage-like lysate comprising Vectors 7, 8, 9, 10A and 10B and the helper phage/lysogen is obtained and transfected into a population of bacteria in which the helper phage will not grow. The inability of the helper phage/lysogen to grow on this population of bacteria can be a result of either the helper phage/lysogen or of the cell it is transfected into. In Example 8, the second strain of bacteria is a lysogen having the same immunity as the helper. Thus, infection by the helper in Example 8 does lyse the cells and the helper does not grow. The present example is directed to other methods of preventing the growth of the helper.

For example, the helper can be conditionally deficient. An example of this embodiment is when the first bacterial cell (i.e., the bacterial cell used for recombination of Vectors 7 and 8) can provide gene O and the helper can be deficient in gene O function. Thus, when the second bacterial population is infected with the phage-like lysate, the conditional deficiency in the helper in gene O will not be complemented and the helper will not grow.

Alternatively, the second bacterial population can overexpress cro. Cro will then bind to the helper genome and give rise to lysogeny, rather than lytic growth of the helper.

Yet another alternative is for the helper phage to contain a temperature sensitivity that is not complemented or mitigated in the second bacterial cell population.

It will therefore be appreciated that any suitable method to prevent the helper phage or lysogen that is present in the phage-like lysate from propagating and entering the lytic cycle in the second population of cells can be used to separate Vector 9 from the helper phage or lysogen.

Example 10

This example illustrates an embodiment of the present inventive method wherein a first vector and a second vector undergo homologous recombination to form a product vector. The first vector employed in this example contains a DSC and does not contain a lambdoid origin of replication.

Figure 12:
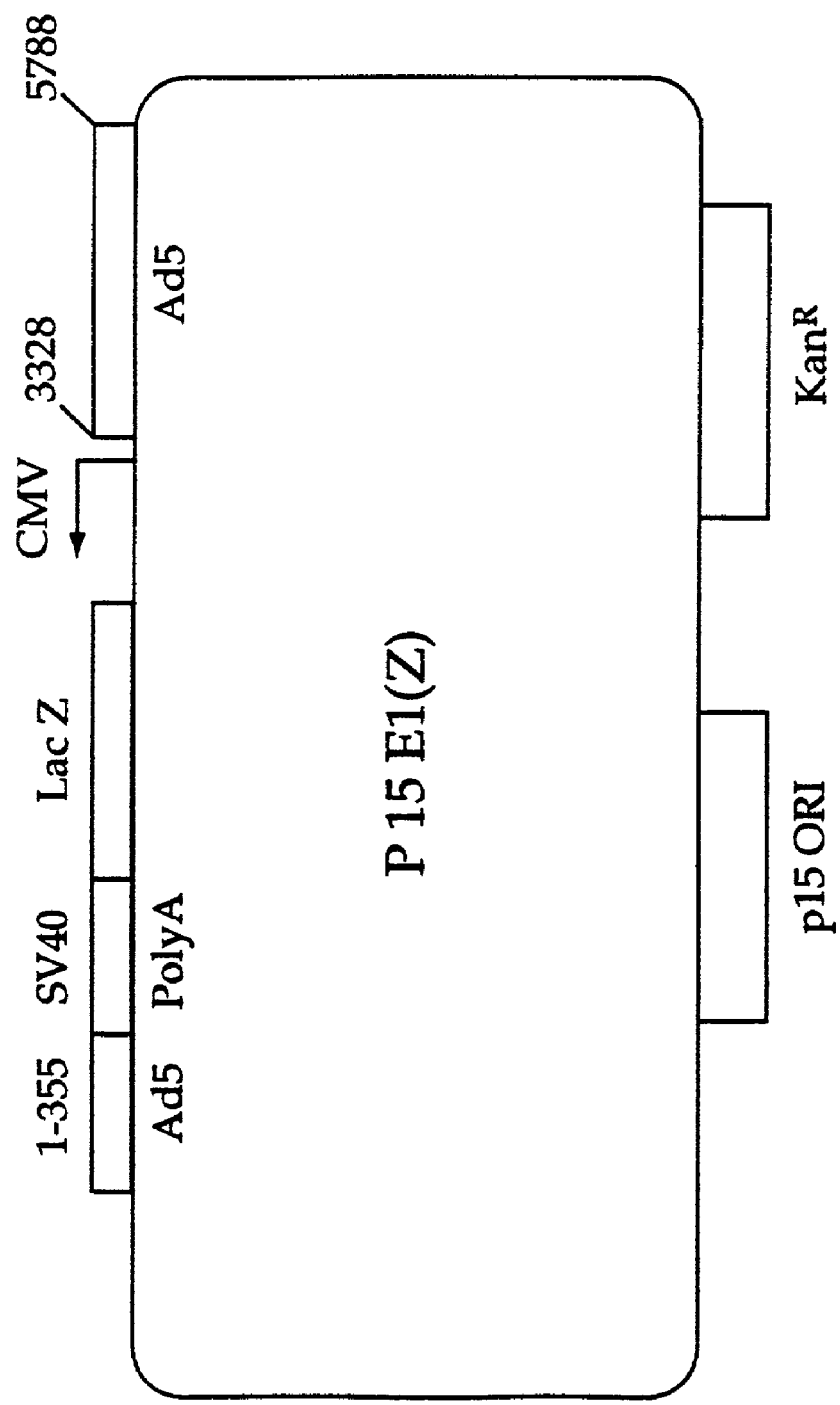
FIG. 12 depicts p15E1(Z). p15E1(Z) is a second vector of the present invention. The plasmid comprises the p15 ori and a kanamycin resistance gene obtained from pACYC177. The bla gene from pACYC 177 was replaced with Ad5 sequences 1 to 5,788. Adenoviral sequences 356 to 3327 were replaced with an expression cassette comprising the CMV promoter operably linked to the Lac Z gene and an SV40 polyadenylation signal.
Figure 13:
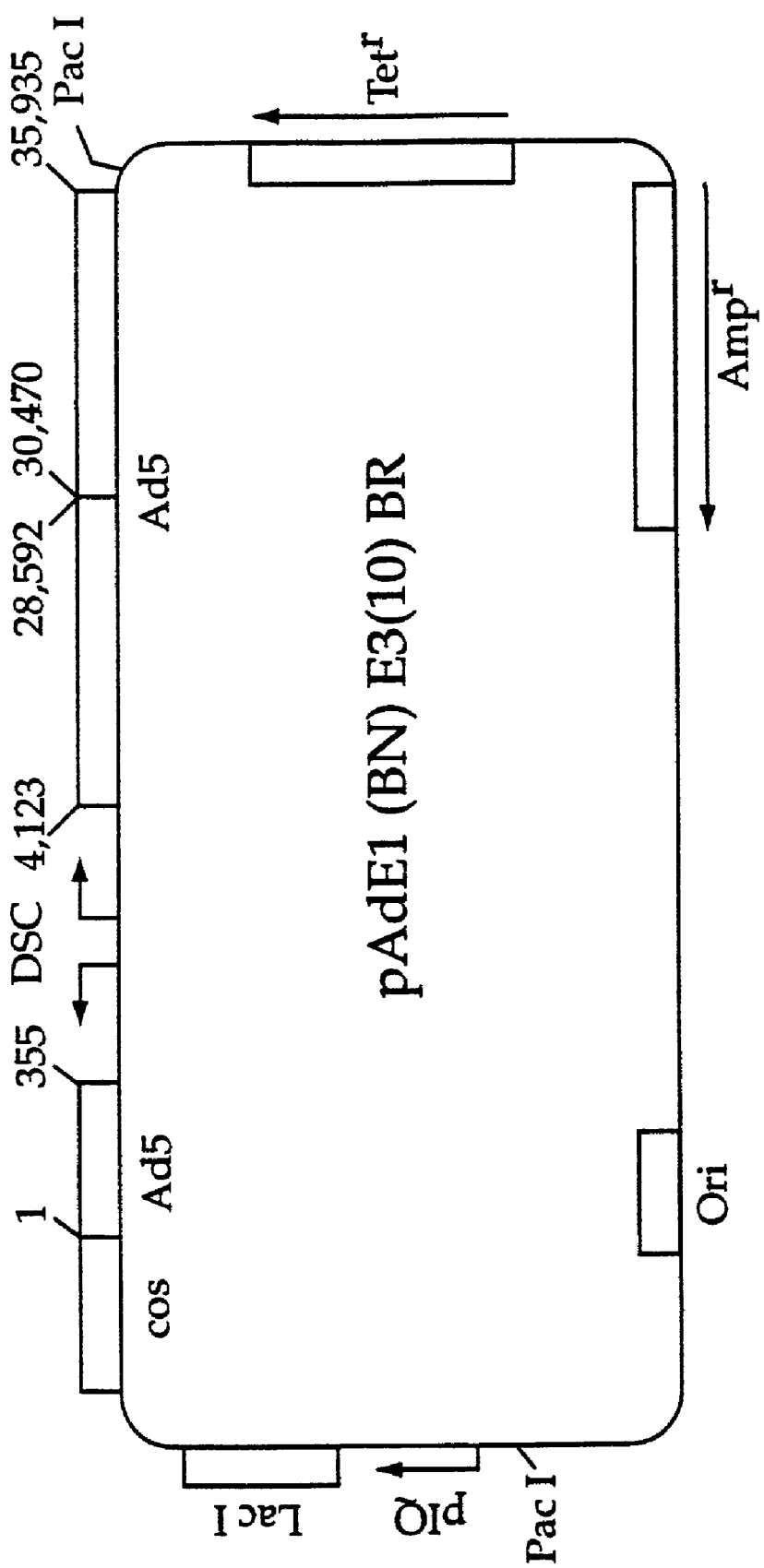
FIG. 13 depicts pAdE1(BN)E310BR and is a pSelect of the present invention. The Sty I site of pBR322 was changed to Pac I. The Lac $I^Q$ expression cassette and a cos site were inserted into the Pac I site. Adjacent to the cos site are adenoviral sequences 1 to 35,935 in which sequences 356 to 4122 are replaced with a DSC and sequences 28,592 to 30,470 (Xba I to Xba I) are deleted. The EM-7 promoter of the DSC is oriented toward the left ITR. The right ITR is next to the Pac I site that is closest to the tetracycline resistance gene.

FIG. 12 depicts p15E1(Z), which is a second vector of the present invention. This plasmid comprises the p15 ori and a kanamycin resistance gene obtained from pACYC177. The bla gene from pACYC177 was replaced with Ad5 sequences 1 to 5,788. Adenoviral sequences 356 to 3327 were replaced with an expression cassette comprising the CMV promoter operably linked to the Lac Z gene and an SV40 polyadenylation signal. p15E1(Z) was co-transfected with pAdE1(BN) E310BR, which is depicted in FIG. 13 (and is a pSelect of the present invention). The Sty I site of pBR322 was changed to Pac I. The Lac I$^Q$ expression cassette and a cos site were inserted into the Pac I site. Adenoviral sequences 1 to 35,935 in which sequences 356 to 4122 are replaced with a DSC and sequences 28,592 to 30,470 (Xba I to Xba I) are deleted were placed adjacent to the cos site. The DSC (of this example) has the following sequence, SEQ ID NO: 6:

```
tcagtcctgc tcctcggcca cgaagtgcac gcagttgccg gccgggtcgc gcagggcgaa   60
ctcccgcccc cacggctgct cgccgatctc ggtcatggcc ggcccggagg cgtcccggaa  120
gttcgtggac acgacctccg accactcggc gtacagctcg tccaggccgc gcacccacac  180
ccaggccagg gtgttgtccg gcaccacctg gtcctggacc gcgtgatgaa cagggtcacg  240
tcgtcccgga ccacacccc gaagtcgtcc tccacgaagt cccgggagaa cccgagccgg  300
tcggtccaga actcgaccgc tccggcgacg tcgcgcgcgg tgagcaccgg aacggcactg  360
gtcaacttgg ccatgacggc gccccattcg ccattcaggc tgcgcaactg ttgggaaggg  420
cgatcggtgc gggcctcttc gctattacgc cagctggcga aaggggggatg tgctgcaagg  480 cgattaagtt gggtaacgcc agggttttcc cagtcacgga cgttgtaaaa cgacggccag  540
tgaattttgc atgcatgcaa aatccgtaat catggccatg gtggccctcc tatagtgagt  600
cgtattatac tatgccgata tactatgccg atgattaatt gtcaacacgt gctgcagccc  660
gggggatccc gcgaaattaa tacgactcac tataggggaga ccacaacggt ttccctctag  720
aaataaattt gtttaacttt aagaaggaga tatacatatg aaaaagacag ctatcgcgat  780
```

-continued

```
tgcagtggca ctggctggtt tcgctaccgt tgcgcaagct gactacaagg acgacgatga 840
caagctggca tttaaatgcc gatccatggt aacctgctac tgtcgtcgta ctcgttgcgg 900
tttccgtgaa cgtctgtccg gtgcttgcgg ttaccgtggt cgtatctacc gtctgtgctg 960
tcgttaa 967
```

TABLE 1

Coordinates of the DSC given in Example 10.
This sequence (SEQ ID NO:6) contains:

| SEQ ID NO:6 | Gene Fragment | Notes |
| --- | --- | --- |
| 1–375 | sch-ble (zeocin resistance) | |
| 385–543 | Lac Z fragment | seqs. 16–174 |
| 562–579 | Lac Z fragment | seqs. 1–18 (fourth base is changed to "G") |
| 580–657 | EM-7 promoter | |
| 672–760 | T7 gene 10 promoter | |
| 758–820 | OmpA signal sequence | |
| 821–844 | Flag epitope | |
| 866–967 | Rat Defensin NP-1 | |

In the vector depicted in FIG. 13, the EM7 promoter of the DSC is oriented toward the left ITR. The right ITR is next to the Pac I site that is closest to the tetracycline resistance gene.

Figure 14:
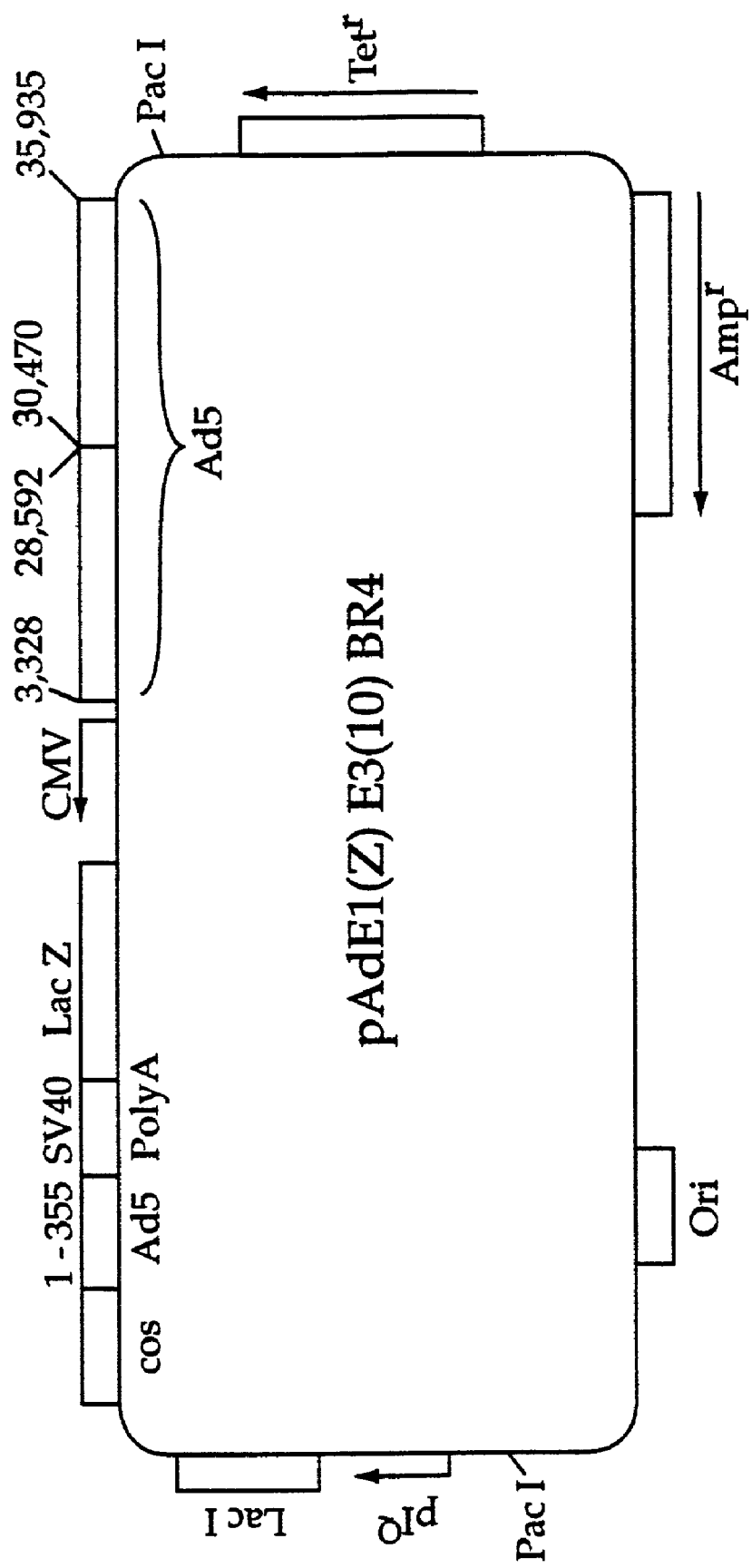
FIG. 14 depicts pAdE1(Z)E3(10)BR, which is a pDesired vector of the present invention. pAdE1(Z)E3(10)BR is isogenic with pAdE1(BN)E310BR except that the Lac Z expression cassette of p15E1(Z) and adenoviral sequences 3328 to 4122 have replaced the DSC.

FIG. 14 depicts pAdE1(Z)E3(11)BR, which is a pDesired vector of the present invention. pAdE1(Z)E3(10)BR is isogenic with pAdE1(BN)E310BR except that the Lac Z expression cassette of p15E1(Z) and adenoviral sequences 3328 to 4122 have replaced the DSC.

pAdE1(BN)E3(10)BR was transformed into DH5α cells and selected on ampicillin. From a saturated culture 100 microliters, 1 microliter, or 10 nanoliters was plated onto both tetracycline containing medium and tetracycline plus IPTG containing medium. The number of surviving colonies is reflected in Table 2 below:

TABLE 2

Susceptibility of DH5α cells to the anti-selective effects of the DSC.

| Volume of Culture | Number of Colonies Formed on Tet | Number of Colonies Formed on Tet + IPTG |
| --- | --- | --- |
| 100 μl | lawn | 13 |
| 1 μl | full plate | 0 |
| 10 nl | 500 | 0 |

There were about 5 million cells in 100 μl of saturated culture. Accordingly, the selective pressure provided by the DSC is sufficient to allow less than 1 in about $10^5$ cells comprising the activated DSC to grow.

Example 11

This example illustrates an embodiment of the present inventive method wherein a first vector and a second vector undergo homologous recombination to form a product vector. The first vector employed in this example contains a DSC and does not contain a lambdoid origin of replication.

Figure 15:
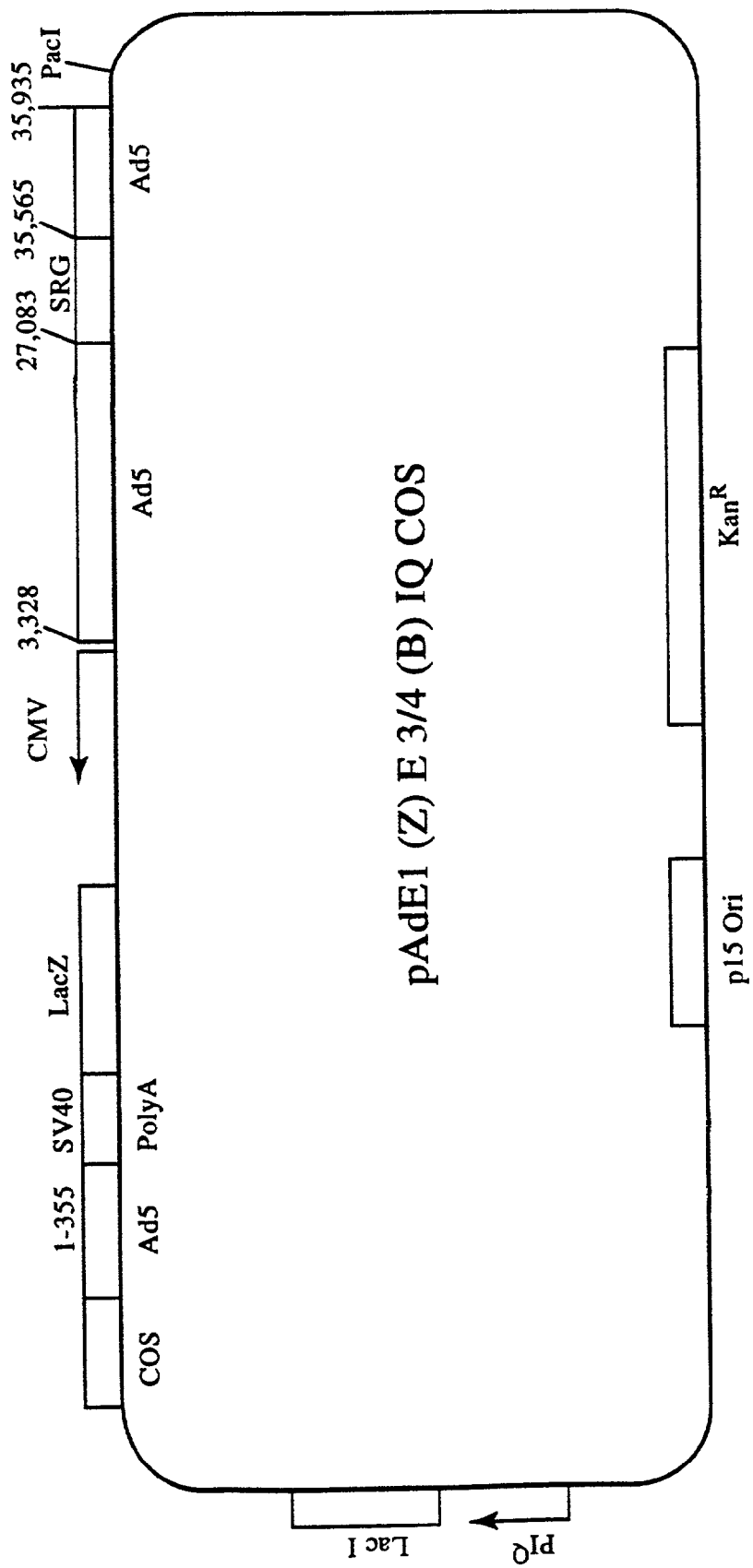
FIG. 15 depicts pAdE1(Z)E¾(B)IQCos, which is a first vector (or pSelect) of the present invention comprising an SRG. This vector comprises a serotype 5 adenoviral genome modified by (i) replacing coordinates 356 to 2,787 with an expression cassette comprising the CMV promoter operably linked to the Lac Z gene and an SV40 polyadenylation sequence, and (ii) replacing coordinates 27,084 to 35,564 with an SRG.

FIG. 15 depicts pAdE1(Z)E¾(B)IQCos, which is a first vector (or pSelect) of the present invention comprising an SRG. This vector comprises a serotype 5 adenoviral genome modified by (i) replacing coordinates 356 to 2,787 with an expression cassette comprising the CMV promoter operably linked to the Lac Z gene and an SV40 polyadenylation sequence, and (ii) replacing coordinates 27,084 to 35,564 with an SRG. The SRG comprises an EM-7 promoter functionally linked to the Lac Z-sch ble gene. The SRG is transcribed toward the right ITR of the adenoviral genome. This vector also comprises a p15 origin of replication, a kanamycin resistance gene, and a Laq $I^Q$ gene located proximally to the cos site. The Laq $I^Q$ gene is transcribed toward the cos site. The cos site is adjacent to the adenoviral left ITR.

The vector pAdE1(Z)E¾(B)IQCos was transformed into a population of BL21(DE3) cells in the presence of kanamycin. The BL21(DE3) cell line is the well known cell line that was made and described in 1986 by Studier and Moffatt. BL21(DE3) cells were made by lysogenising an E. coli with lambda 21 phage carrying T7 RNA polymerase under the LacUV5 promoter. Consequently, BL21(DE3) cells overexpress T7 RNA polymerase when exposed to IPTG. Various volumes of a saturated culture of the transformed BL21 (DE3) cells were plated on a 10 cm agarose plate comprising suitable quantities of kanamycin and IPTG. After maintaining the cells at 37° C. for 16 hours, 100 microliters of culture gave rise to 50 colonies, however, 1 microliter of culture gave rise to only 3 secondary or pin point colonies, and 10 nanoliters of culture resulted in no colonies. In contrast, when plated on kanamycin only, 100 microliters of culture resulted in a lawn, 1 microliter resulted in distinct colonies lacking substantial space between colonies (i.e., the plate was overloaded or full of colonies), and 10 nanoliters of culture resulted in about 200 colonies. These results demonstrate that less than about 1 in $10^4$ bacteria comprising the SRG of pAdE1(Z)E¾(B)IQCos are able to survive or effectively grow in the presence of T7 RNA polymerase.

Example 12

This example illustrates that the present inventive method provides an efficient and straightforward method of making a recombinant DNA vector via homologous recombination.

The bacterial strain LE392 was co-transformed with pAdE1(BN)E3(10)BR and p15E1(Z) and maintained under selective pressure for ampicillin and kanamycin. Using standard techniques, a phage lysate was made from the transformed LE392 culture with lambda clear. A portion of the lysate (100 μl) was used to infect the cells of 1 ml of an saturated culture of a DH5α/lambda lysogen. Serial dilutions of the infected lysogen culture were plated under selective pressure for kanamycin, or ampicillin, tetracycline and IPTG. Table 3 shows the number of colonies obtained under each condition.

TABLE 3

Number of colonies observed.

| Volume of Culture Plated | Number of Colonies Observed on Kanamycin | Number of Colonies Observed on Ampicillin, Tetracycline, and IPTG |
|---|---|---|
| 1000 nl | 1530 | 170 |
| 10 nl | 300 | 1 |

These results demonstrate that between about 0.1% and 0.4% of the single homologous recombination events were resolved by a second homologous recombination event to produce the desired product vector. This result was confirmed by re-plating the colonies. Of the re-plated colonies 94% were found to be sensitive to kanamycin and resistant to ampicillin. Seventeen of eighteen colonies had the expected pattern of DNA fragmentation when isolated DNA was restriction digested with Hind III and Pac I. These results demonstrate that the present inventive vectors and methods enable the production of a recombinant DNA vector using homologous recombination (single and double) to generate product vectors with an efficiency of at least about 5%, and preferably with an efficiency of at least about 80%.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of making a DNA comprising a recombinant eukaryotic viral amplicon, the method comprising:
    (a) transducing a bacterial cell with a first DNA, wherein the first DNA comprises a DNA vector comprising (i) a portion of eukaryotic viral genome comprising an ITR, (ii) a regulatable anti-selection gene, (iii) a phage packaging site, and (iv) a deficient or conditionally-deficient lambdoid origin of replication, and a second DNA, which comprises a DNA segment with high homology to a DNA segment of the first DNA, and
    (b) transducing the bacterial cell with a defective phage or a non-defective phage, or activating a defective or non-defective lysogen within the cell, such that the deficient or conditionally-deficient lambdoid origin of replication is operable and the first DNA and the second DNA undergo a double homologous recombination event to form a DNA comprising a recombinant eukaryotic viral amplicon.

2. The method of claim 1, wherein the defective lysogen, non-defective lysogen, defective phage, or non-defective phage is lambda clear.

3. The method of claim 1, wherein the defective lysogen, non-defective lysogen, defective phage, or non-defective phage has a geziome and a phage packaging site, wherein the phage packaging site of the defective lysogen, non-defective lysogen, defective phage, or non-defective phage is missing or can be rendered non-functional without isolating the genome of the defective lysogen, non-defective lysogen, defective phage, or non-defective phage.

4. The method of claim 3, wherein the phage packaging sequence is flanked by parallel site-directed homologous recoxubination sites and wherein the bacterial cell expresses a site-directed homologous recombinase.

5. The method of claim 4, wherein the site-directed homologous recombination sites are lox sites and the site-directed homologous recombinase is cre.

6. A method of making a desired vector comprising a desired eukaryotic viral amplicon, the method comprising:
    (i) transforming a first bacterial cell under conditions that are permissive of homologous recombination with a first DNA, which comprises (a) a phage packaging site, (b) a conditionally-deficient lambdoid origin of replication, (c) an independent positive selection gene, and (d) a eukaryotic viral DNA with an anti-selective gene embedded in the eukaryotic viral DNA, and a second DNA, which comprises two DNA sequences with high homology to the first DNA flanking a DNA sequence of interest, wherein (d) does not comprise (a),
    (ii) expressing in the first bacterial cell a source of phage gene functions that provides for the operation of the conditionally-deficient lambdoid origin of replication and that encansidates vectors comprising a suitable length of DNA and the phage packaging site, wherein the source is an activated lysogen or a superinfected phage, to obtain a mixed population of encapsidated vectors, the mixed population comprising a desired lambdid vector that comprises a desired eukaryotic viral arnplicon,
    (iii) obtaining a phage-like lysate of the mixed population of encapsidated vectors,
    (iv) transducing a second bacterial cell with the phage-like lysate, and
    (v) maintaining the second bacteria cell under conditions selective for the first independent positive selection gene and anti-selective for the superinfected phage and the anti-selective gene, to isolate a colony comprising a desired vector comprising a desired eukaryotic viral amplicon.

* * * * *

SEQUENCE LISTING

<160> NUMBER OF SEQ ID NOS: 6

<210> SEQ ID NO 1
<211> LENGTH: 467
<212> TYPE: DNA
<213> ORGANISM: Artificial Sequence
<220> FEATURE:
<223> OTHER INFORMATION: Synthetic DNA

<400> SEQUENCE: 1

```
tacgcgcatt gcaaatgagt tgctggaagc tgtgatgctg gccggattaa cacagcacca      60
gcttctggtc ttcctggctg tcatgcgcaa aacatatggc tttaataaaa aactggattg     120
ggtgagcaac gagcaacttt ccgagttgac cgggatattg ccgcacaagt gttctgctgc     180
aaaaagcgtt ctggtaaagc gtgggattct tattcagagc gggcggaata tcggcattaa     240
taatgtggtc agtgaatggt caacattacc cgaatcaggt aagaaaaata aagtttacct     300
gaaagaggta aatttacctg aatcaggtaa aaaaagtttta cccaaatcag gtaaaggcgt     360
ttacccgaat caggtaaaca caaagacaa actaacaaaa gacaatataa aaccttttttc     420 gtccgagaat tctggcgaat cctctgacca accagaaaac gatcttc                    467
```

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Gly Ser Gly Ser Gly Ser Gly Ser Gly Ser Ala Cys Asp Cys Arg Gly
1               5                   10                  15

Asp Cys Phe Cys Gly
            20

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

```
<400> SEQUENCE: 3

Gly Ser Gly Ser Gly Ser Gly Ser Gly Ser Lys Lys Lys Lys Lys
1               5                   10                  15
Lys

<210> SEQ ID NO 4
<211> LENGTH: 69
<212> TYPE: DNA
<213> ORGANISM: Artificial Sequence
<220> FEATURE:
<223> OTHER INFORMATION: Synthetic DNA

<400> SEQUENCE: 4
gtggaagaga tctatagcgg tagcggcagc ggtagcgcgt gcgattgtcg tggtgattgc    60
ttctgcggc                                                           69

<210> SEQ ID NO 5
<211> LENGTH: 23
<212> TYPE: PRT
<213> ORGANISM: Artificial Sequence
<220> FEATURE:
<223> OTHER INFORMATION: Synthetic peptide

<400> SEQUENCE: 5

Val Glu Glu Ile Tyr Ser Gly Ser Gly Ser Gly Ser Ala Cys Asp Cys
1               5                   10                  15

Arg Gly Asp Cys Phe Cys Gly
            20

<210> SEQ ID NO 6
<211> LENGTH: 967
<212> TYPE: DNA
<213> ORGANISM: Artificial Sequence
<220> FEATURE:
<223> OTHER INFORMATION: Synthetic DNA

<400> SEQUENCE: 6
tcagtcctgc tcctcggcca cgaagtgcac gcagttgccg gccgggtcgc gcagggcgaa    60
ctcccgcccc cacggctgct cgccgatctc ggtcatggcc ggcccggagg cgtcccggaa   120
gttcgtggac acgacctccg accactcggc gtacagctcg tccaggccgc gcacccacac   180
ccaggccagg gtgttgtccg gcaccacctg gtcctggacc gcgtgatgaa cagggtcacg   240
tcgtcccgga ccacaccccc gaagtcgtcc tccacgaagt cccgggagaa cccgagccgg   300
tcggtccaga actcgaccgc tccggcgacg tcgcgcgcgg tgagcaccgg aacggcactg   360
gtcaacttgg ccatgacggc gccccattcg ccattcaggc tgcgcaactg ttgggaaggg   420
cgatcggtgc gggcctcttc gctattacgc cagctggcga aggggggatg tgctgcaagg   480
cgattaagtt gggtaacgcc agggttttcc cagtcacgga cgttgtaaaa cgacggccag   540
tgaattttgc atgcatgcaa atccgtaat catggccatg gtgccctcc tatagtgagt    600 cgtattatac tatgccgata ctatgccg atgattaatt gtcaacacgt gctgcagccc    660
gggggatccc gcgaaattaa tacgactcac tatagggaga ccacaacggt ttccctctag   720
aaataatttt gtttaacttt aagaaggaga tatacatatg aaaagacag ctatcgcgat    780 tgcagtggca ctggctggtt tcgctaccgt tgcgcaagct gactacaagg acgacgatga   840
```

-continued

```
caagctggca tttaaatgcc gatccatggt aacctgctac tgtcgtcgta ctcgttgcgg     900
tttccgtgaa cgtctgtccg gtgcttgcgg ttaccgtggt cgtatctacc gtctgtgctg     960
tcgttaa                                                               967
```